(12) United States Patent
Tamakoshi et al.

(10) Patent No.: US 6,972,425 B2
(45) Date of Patent: Dec. 6, 2005

(54) RADIATION IMAGE RADIOGRAPHING SYSTEM

(75) Inventors: Yasuaki Tamakoshi, Sayama (JP); Masayuki Nakagawa, Hino (JP); Hisashi Yonekawa, Hino (JP); Yuhei Okamoto, Tokyo (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 10/931,782

(22) Filed: Sep. 1, 2004

(65) Prior Publication Data

US 2005/0023495 A1 Feb. 3, 2005

Related U.S. Application Data

(63) Continuation of application No. 09/989,515, filed on Nov. 20, 2001, now Pat. No. 6,806,487.

(30) Foreign Application Priority Data

Nov. 24, 2000 (JP) .............................. 2000-356933

(51) Int. Cl.[7] ........................ G03B 42/02; G01T 1/161; A61B 6/00
(52) U.S. Cl. ...................... 250/583; 250/581; 250/580; 250/369; 705/3; 709/217; 370/221
(58) Field of Search ................................ 250/583, 581, 250/580, 369; 705/3; 709/217; 370/221

(56) References Cited

U.S. PATENT DOCUMENTS

| | | | |
|---|---|---|---|
| 4,789,782 A | | 12/1988 | Ohara |
| 5,592,374 A | * | 1/1997 | Fellegara et al. ............... 705/3 |
| 5,646,416 A | | 7/1997 | Van de Velde |
| 5,654,555 A | * | 8/1997 | Buytaert et al. ............ 250/581 |
| 5,655,084 A | * | 8/1997 | Pinsky et al. ................... 705/3 |
| 5,757,021 A | * | 5/1998 | Dewaele ...................... 250/581 |
| 5,865,745 A | * | 2/1999 | Schmitt et al. .............. 600/407 |
| 5,911,687 A | * | 6/1999 | Sato et al. ................... 600/300 |
| 6,047,257 A | * | 4/2000 | Dewaele ...................... 704/270 |
| 6,078,947 A | * | 6/2000 | Kagermeier ................ 709/203 |
| 6,260,021 B1 | * | 7/2001 | Wong et al. .................... 705/2 |
| 6,359,628 B1 | * | 3/2002 | Buytaert et al. ............ 345/619 |
| 6,501,827 B1 | * | 12/2002 | Takasawa .................... 378/116 |
| 6,574,629 B1 | * | 6/2003 | Cooke et al. ................. 707/10 |
| 6,598,011 B1 | * | 7/2003 | Howards Koritzinsky et al. ......... 702/185 |
| 6,762,429 B2 | * | 7/2004 | Aonuma ...................... 250/583 |
| 6,859,288 B1 | * | 2/2005 | Brackett et al. ........... 358/1.15 |
| 6,859,511 B2 | * | 2/2005 | Kamimura et al. ............. 378/4 |
| 2002/0028007 A1 | * | 3/2002 | Gendron et al. ............ 382/128 |
| 2002/0113590 A1 | * | 8/2002 | Haworth et al. ............ 324/309 |
| 2002/0122211 A1 | | 9/2002 | Aonuma |

(Continued)

FOREIGN PATENT DOCUMENTS

EP 0 674 187 A1 9/1995

(Continued)

Primary Examiner—Albert Gagliardi
(74) Attorney, Agent, or Firm—Frishauf, Holtz, Goodman & Chick, P.C.

(57) ABSTRACT

The invention concerns a network system for radiographing radiation images. The network system includes a plurality of radiation-image reading apparatus to read the radiation images stored in radiation-image storing sheets, so as to generate image data sets each of which corresponds to each of the radiation images, and a plurality of controllers to register discrimination information sets each of which corresponds to each of the radiation-image storing sheets. Each of the controllers can display a radiation image for confirmation, when it receives an image data set corresponding to the radiation image. A radiation-image reading apparatus reads a discrimination information set recorded on a radiation-image storing sheet loaded into the radiation-image reading apparatus.

14 Claims, 12 Drawing Sheets

U.S. PATENT DOCUMENTS

2002/0184325 A1 * 12/2002 Killcommons et al. ..... 709/206

FOREIGN PATENT DOCUMENTS

| EP | 0 849 933 A2 | 6/1998 |
| EP | 0 905 637 A1 | 3/1999 |
| EP | 0 919 857 A2 | 6/1999 |
| JP | 11-161729 A | 6/1999 |

* cited by examiner

RADIATION IMAGE RADIOGRAPHING SYSTEM

CROSS-REFERENCE TO RELATED APPLICATIONS

The present application is a Continuation Application of U.S. application Ser. No. 09/989,515, filed Nov. 20, 2001, now U.S. Pat. No. 6,806,487.

BACKGROUND OF THE INVENTION

The present invention mainly relates to a radiation-image radiographing system comprising a radiation-image reading apparatus to output the digitized image data, and controllers.

Recently, there is a strong tendency to increase the efficiency and speed of the diagnosis by digitizing radiation image information of a patient generated in a hospital and by storing and electrically transmitting it. Therefore, in the field of the direct radiographing, instead of the conventional screen/film system, a radiation-image radiographing system to output the digital data utilizing the stimulable phosphor substance is frequently used.

This radiation-image radiographing system utilizing this stimulable phosphor substance is called a common name computed radiography (CR). In this apparatus, a part of the radiographic energy transmitted through a subject is stored once in the stimulable phosphor substance. The energy stored in the stimulable phosphor substance can be taken out as the stimulative light by exciting it by the predetermined wavelength laser light. This stimulaitve light can be taken out as an electric signal by using a photoelectric conversion element such as a photo-multiplier.

The radiation-image radiographing system can be largely classified into an exclusive type radiation-image radiographing system which can not so simply be carried, in which the stimulable phosphor substance is housed, and a cassette type radiation-image radiographing system using a cassette in which the stimulable phosphor substance is housed, and which can be carried.

Referring to FIG. 1 showing the cassette type radiation-image radiographing system using the stimulable phosphor substance, the cassette type radiation-image radiographing system using the stimulable phosphor substance will be described below. A cassette 6 is portable one in which a stimulable phosphor substance sheet 8 storing a portion of the radiographic energy is housed. In a radiographing room, a subject M is positioned between a radiographic tube 9 and the cassette 6, and the radioactive ray from the radiographic tube 9 is irradiated toward the cassette 6. The stimulable phosphor substance sheet 8 in the cassette 6 stores a part of the irradiated radiographic energy.

Then, when the cassette 6 is set to a radiation-image reading apparatus 1, the radiation-image reading apparatus 1 reads out the radiation image information stored in the stimulable phosphor substance sheet 8. Further, a controller 2 has a monitor for which the patient information and the information such as a radiographing portion relating to the image stored on the cassette 6, is inputted and by which the read-out image by the radiation-image reading apparatus 1 is confirmed.

Then, the radiation-image reading apparatus 1, in order to read-out the radiation image information stored in the stimulable phosphor substance sheet 8 in the cassette 6, irradiates the excitation light onto the stimulable phosphor substance sheet and photoelectric converts the stimulative light emitted corresponding to the radiation image information stored by the irradiated excitation light, and after A/D conversion, outputs as the digital image data, however, the high accuracy is required for these systems, and the cost is considerably high.

Further, in order to enable to simultaneously set a plurality of cassettes of sheets of film, which are photographed in the inspection of one time, the radiation-image reading apparatus 1 is large sized.

Then, conventionally, in such the cassette type radiation-image radiographing system, the radiation-image reading apparatus 1 and its exclusive controller 2 are integrated, or separately connected in 1 to 1. Accordingly, in many cases, one set of radiation-image reading apparatus 1 and its exclusive controller 2 are installed per a plurality of radiographing rooms. However, the radiographing operation in the radiographing room in which this set is not installed, is inconvenient, and because the time interval between the radiographing and the input of the patient information and radiographing information is long, the input mistake of the radiographic engineer tends to occur.

Further, because the time until the engineer goes to the radiation-image reading apparatus 1 from the radiographing room, and sets the cassette and returns to the radiographing room after the image confirmation, becomes long, there is a problem that the instruction of the next radiographing can not be given to the patient between the time, or as the result of the image confirmation after the photographed patient goes out of the radiographing room, when the re-radiographing is necessary, the calling out becomes necessary. Accordingly, although it is considered that at least one set of the radiation-image reading apparatus 1 and its exclusive controller 2 is installed in each radiographing room in the hospital, because it is installed irrespective of the frequency of the radiographing in the radiographing room, it is uneconomical, and further, the mounting space becomes large, and the cost is high.

Further, in any case, there is a problem, when any one of the radiation-image reading apparatus 1 or its controller 2 is faulty, both of them cannot be used.

Further, as another system from said radiographic photographic system, a system shown in FIG. 2 is proposed. In this system, simultaneously when the patient information of the patient to be photographed by the cassette 6, and the information of a photographic position is inputted at the information input terminal 5, the ID number to discriminate the stimulable phosphor substance sheet 8 accommodated in the cassette 6 is read out, and as a series of information corresponding to the patient information or radiographing position information, it is stored in the server 4 through the network 3. When the patient radiographing using the cassette 6 is completed, the cassette 6 is set to the radiation-image reading apparatus 1, and in the same manner as the radiation-image reading apparatus 1, the radiation image information stored in the stimulable phosphor substance sheet 8 in the set cassette 6 is read out. At the time, by the radiation-image reading apparatus 1, the ID number of the stimulable phosphor substance sheet 8 is also read out. The radiation-image reading apparatus 1 refers the registration information corresponding to the read out ID number to the server 4. The radiation-image reading apparatus 1 makes correspondence of the registration information answered from the server 4 with the read out radiation image information, and transfers it to an image confirmation apparatus 7.

Because the registration information and the radiation image information from a plurality of radiation-image reading apparatus 1 are collected in the image confirmation apparatus 7, the final confirmation of the image is conducted therein.

In this system, a plurality of information input terminals 5 and radiation-image reading apparatus 1 are connected to the network 3. In each radiographing room of the hospital, only the information input terminal 5 is installed, and when, in a common space between the radiographing rooms, a plurality of radiation-image reading apparatus 1 are installed, the installation space can be more reduced.

However, in each radiographing room, because the image confirmation apparatus 7 is not installed, there is a problem that the radiologist who is charge of radiographing cannot confirm the image. Accordingly, a full-time person who uses the image confirmation apparatus 7 and conducts the image confirmation, is necessary, and there is a defect, which results in an increase of the human cost.

Further, when the image confirmation apparatus 7 is malfunctioned, there is a defect that the image read out by whole radiation-image reading apparatus 1 cannot be confirmed.

Accordingly, it is considered that the image confirmation apparatus 7 is installed in each radiographing room. According to this, when a nurse or an assistant goes to set the cassette 6 to the radiation-image reading apparatus 1, the radiologist can input the patient information or radiographing information or confirm the image, without going-out from the radiographing room. However, when the information input terminal 5 and the image confirmation apparatus 7 are installed in each radiographing room, there is a problem that a large installation space is necessary, and the wiring easily becomes complicated.

Further, because it is necessary that both of the information input terminal 5 and the image confirmation apparatus 7 are installed in each radiographing room, the cost is increased. Further, because it is necessary that the radiologist operates both of the controller 2 and the image confirmation apparatus 7, the operation efficiency is lowered.

Further, because the images photographed in other radiographing rooms are returned to the image confirmation apparatus 7, it takes a long period of time to find out his own photographed image. In order to avoid this problem, in the case where the image confirmation apparatus 7 is directly connected to respective radiation-image reading apparatus 1, when either one of the radiation-image reading apparatus 1 or the image confirmation apparatus 7 is faulty, a new problem that both of them can not be used, is generated.

SUMMARY OF THE INVENTION

To overcome the abovementioned problems, it is an object of the present invention to provide a radiation-image radiographing system in which the radiologist can input the patient information relating to the radiographing and reading or the radiographing information, or can conduct the image confirmation or the change of the image processing, at a position near the site of the radiographing, and to the user, the operation efficiency is good and an easily operable circumstance can be provided, and the installation area of the apparatus is reduced, and the introduction cost is low and the expandability is high. Further, another object of the present invention is to provide a system in which, even when a portion of the component is faulty, the other component can correspond to that, and which is easily operable and whose reliability is high.

Accordingly, to overcome the cited shortcomings, the abovementioned objects of the present invention can be attained by network systems described as follow.

(1) A network system for radiographing radiation images, comprising: a plurality of radiation-image reading apparatus to read the radiation images stored in radiation-image storing sheets so as to generate image data sets each of which corresponds to each of the radiation images; and a plurality of controllers to register discrimination information sets each of which corresponds to each of the radiation-image storing sheets; wherein said plurality of radiation-image reading apparatus and said plurality of controllers are coupled each other to form said network system, and each of the controllers can display a radiation image for confirmation, when it receives an image data set corresponding to the radiation image, the radiation image being one of the radiation images and the image data set being one of the image data sets; and wherein a radiation-image reading apparatus reads a discrimination information set recorded on a radiation-image storing sheet loaded into the radiation-image reading apparatus, in order to specify a controller, which registered the discrimination information set of the radiation-image storing sheet, on the basis of the discrimination information set, so as to transmit the image data set, read from the radiation-image storing sheet, to the controller specified by the radiation-image reading apparatus, and the radiation-image reading apparatus, the discrimination information set, the radiation-image storing sheet and the controller are one of the plurality of radiation-image reading apparatus, one of the discrimination information sets, one of the radiation-image storing sheets and one of the plurality of controllers, respectively.

(2) The network system of item 1, wherein the radiation-image storing sheet can be loaded into any one of the plurality of radiation-image reading apparatus, even if any one of the plurality of controllers registers the discrimination information set of the radiation-image storing sheet.

(3) The network system of item 1, wherein, when the image data set read from the radiation-image storing sheet cannot be transmitted to the controller specified by the radiation-image reading apparatus, the image data set is transmitted to another controller, being one of the plurality of controllers.

(4) The network system of item 1, wherein each of the controllers comprises an acquiring section to acquire identification data of an operator who controls a controller concerned, and registers the discrimination information set of the radiation-image storing sheet in conjunction with the identification data of the operator; and wherein, when the image data set read from the radiation-image storing sheet cannot be transmitted to the controller specified by the radiation-image reading apparatus, the image data set is transmitted to another controller in which the acquiring section acquires the identification data of the operator coinciding with that in respect to the image data set.

(5) The network system of item 1, wherein each of the controllers registers the discrimination information sets of the radiation-image storing sheets in respect to a subject in conjunction with subject's identification data, and displays a predetermined message, when it receives the image data sets read from all of the radiation-image storing sheets in respect to the subject.

(6) The network system of item 1, wherein each of the controllers can change an order of the image data sets read from the radiation-image storing sheets in respect to a subject when outputting the image data sets.

(7) The network system of item 1, further comprising: a database section to store a database of recording files, each of which includes the discrimination information set registered by the controller and controller-discrimination information set corresponding to the controller; wherein the database section retrieves the discrimination information set from any one of the plurality of radiation-image reading apparatus and returns a recording file concerned, being one of the recording files, and then, the radiation-image reading apparatus specifies a controller, which registered the discrimination information set of the radiation-image storing sheet, on the basis of the discrimination information set included in the recording file, so as to transmit the image data set, read from the radiation-image storing sheet, to the controller specified by the radiation-image reading apparatus.

(8) The network system of item 2, further comprising: a database section to store a database of recording files, each of which includes the discrimination information set registered by the controller and controller-discrimination information set corresponding to the controller; wherein the database section retrieves the discrimination information set from any one of the plurality of radiation-image reading apparatus and returns a recording file concerned, being one of the recording files, and then, the radiation-image reading apparatus specifies a controller, which registered the discrimination information set of the radiation-image storing sheet, on the basis of the discrimination information set included in the recording file, so as to transmit the image data set, read from the radiation-image storing sheet, to the controller specified by the radiation-image reading apparatus.

(9) The network system of item 1, wherein the controller can transmit a recording file, including the discrimination information set registered by the controller and a controller-discrimination information set corresponding to the controller, to all of the plurality of radiation-image reading apparatus, and the radiation-image reading apparatus stores the recording file and transmits the image data set, on the basis of the controller-discrimination information set included in the recording file coinciding with the discrimination information set of the radiation-image storing sheet.

(10) The network system of item 1, wherein the radiation-image reading apparatus retrieves a coincided recording file in respect to all of the plurality of controllers by utilizing the discrimination information set of the radiation-image storing sheet, and transmits the image data set read from the radiation-image storing sheet to a controller having the coincided recording file.

(11) The network system of item 1, wherein each of the controllers also registers a radiographing information set including data, such as a body part of a subject to be radiographed, a radiographing direction, radiographing conditions, etc., in addition to the discrimination information set of the radiation-image storing sheet currently utilized for radiographing the subject, and the controller determines a reading condition for reading the radiation-image storing sheet on the basis of the radiographing information set registered by the controller; and wherein the radiation-image reading apparatus acquires the reading condition on the basis of the discrimination information set of the radiation-image storing sheet, and reads a radiation image stored in the radiation-image storing sheet under the reading condition acquired, so as to generate the image data set.

(12) The network system of item 1, wherein each of the controllers also registers a radiographing information set including data, such as a body part of a subject to be radiographed, a radiographing direction, radiographing conditions, etc., in addition to the discrimination information set of the radiation-image storing sheet currently utilized for radiographing the subject; and wherein the controller applies an image-processing onto the image data set received in conjunction with the discrimination information set of the radiation-image storing sheet on the basis of the radiographing information set, which coincides with the discrimination information set, so as to output an image-processed image data set.

(13) The network system of item 1, wherein each of the controllers controls an exclusive type radiation-image reading apparatus, and receives an image data set outputted by the exclusive type radiation-image reading apparatus, synchronizing with a radiographing operation performed by the exclusive type radiation-image reading apparatus.

Further, to overcome the abovementioned problems, other radiation-image radiographing systems, embodied in the present invention, will be described as follow:

(14) A radiation-image radiographing system in which a plurality of controllers to register a discrimination information (also referred to as a discrimination information set) of a radiation-image storing sheet, and a plurality of radiation-image reading apparatus to read the radiation image stored in the radiation-image storing sheet and output an image data (also referred to as an image data set) are arranged on the same network, wherein, when the controller receives the image which is read from the radiation-image storing sheet by the radiation-image reading apparatus, the controller can display the image for confirmation, and even the radiation-image storing sheet whose discrimination information is registered by any one of the plurality of controllers, can be set to any one of the plurality of radiation-image reading apparatus, and the radiation-image reading apparatus reads the discrimination information of the set radiation-image storing sheet, and even any one of the plurality of the radiation-image reading apparatus, according to the discrimination information read by the radiation-image reading apparatus, specifies the controller in which the discrimination information of the radiation-image storing sheet is registered, and try to transmit the radiation image which is read from the radiation-image storing sheet by the radiation-image reading apparatus, to the specified controller.

(15) A radiation-image radiographing system according to item 14, wherein, in the case where the radiation image which is read from the radiation-image storing sheet by the radiation-image reading apparatus, is tried to be transmitted to the specified controller, when the transmission to the controller can not be carried out, the image is tried to be transmitted to another controller.

(16) A radiation-image radiographing system according to item 15, wherein all of the plurality of controllers have a means (also referred to as an acquiring section) for obtaining the discrimination information proper to an operator (also referred to as identification data of an operator) of the controller, and when the controller registers the discrimination information of the radiation-image storing sheet, the discrimination information proper to the operator of the controller is also registered together with it, and in the case where the radiation-image reading apparatus tries to transmit the radiation image read from the radiation-image storing sheet by the radiation-image reading apparatus to the specified controller, when the transmission to the controller can not be carried out, it is tried to be transmitted to the controller, in other controllers, with which the discrimination information proper to the operator coincides.

(17) A radiation-image radiographing system according to any one of items 14–16, wherein, when the discrimination information of a plurality of radiation-image storing sheets relating to one subject are registered, the discrimination information proper to the subject (also referred to as subject's identification data) can also be registered together with it, and in the case where the discrimination information of the plurality of radiation-image storing sheets relating to the one subject, are registered, when the discrimination information proper to the subject is registered together with it, in the case where all of the image which is read from the plurality of radiation-image storing sheets relating to the one subject, are received, any display is carried out.

(18) A radiation-image radiographing system according to any one of items 14–17, wherein the controller can arrange images read from the plurality of radiation-image storing sheets in a predetermined order and output them.

(19) A radiation-image radiographing system according to any one of items 14–18, wherein it has, on the same network, a data base means (also referred to as a database section) for storing the data base of the record including the discrimination information of the radiation-image storing sheets registered by at least the plurality of controllers and the discrimination information of the controller in which the discrimination information is registered, and the data base means can be searched by the discrimination information of the radiation-image storing sheet from any one of the plurality of radiation-image reading apparatus, and the corresponding record is returned, and according to the discrimination information of the controller of the returned record, each one of the plurality of the radiation-image reading apparatus specifies the controller registered relating to the radiation-image storing sheet, and tries to transmit the radiation image read from the radiation-image storing sheet by the radiation-image reading apparatus to the specified controller.

(20) A radiation-image radiographing system according to any one of items 14–18, wherein any one the plurality of controllers transmits the discrimination information of the radiation-image storing sheet registered by the controller and the record including the discrimination information of the controller (also referred to as a controller-discrimination information set) to all of the plurality of the radiation-image reading apparatus, and any one of the plurality of the radiation-image reading apparatus stores the received record, and according to the discrimination information of the controller of the record which coincides with the discrimination information of the read radiation-image storing sheet, tries to transmit the read image.

(21) A radiation-image radiographing system according to any one of items 14–18, wherein any one of the plurality of radiation-image reading apparatus searches the record which coincides with the discrimination information of the radiation-image storing sheet to all of the plurality of the controllers, by the read discrimination information of the radiation-image storing sheet, and to the controller which has the coincidence record, tries to transmit the read image.

(22) A radiation-image radiographing system according to any one of items 14–21, wherein, when the discrimination information of the radiation-image storing sheet is registered by the controller, the radiographing information relating to the radiographing position of the subject to be photographed by the radiation-image storing sheet, or the radiographing direction or radiographing condition is also registered with together, and the controller determines the reading condition of the radiation-image storing sheet according to the registered radiographing information, and the radiation-image reading apparatus obtains the reading condition according to the discrimination information of the read radiation-image storing sheet, and according to the obtained reading condition, the image data is read from the radiation-image storing sheet.

(23) A radiation-image radiographing system according to any one of items 14–22, wherein, when the discrimination information of the radiation-image storing sheet is registered by the controller, the radiographing information relating to the radiographing position of the subject to be photographed by the radiation-image storing sheet, or the radiographing direction or radiographing condition is also registered with together, and the controller image processes the image data received together with the discrimination information of the radiation-image storing sheet, and outputs it, according to the radiographing information which coincides with the discrimination information of the radiation-image storing sheet.

(24) A radiation-image radiographing system according to any one of items 14–23, wherein the controller can control the exclusive type photographic image reading apparatus, and the image data outputted from the exclusive type radiation-image reading apparatus can be received synchronously with the radiographing by the exclusive type radiation-image reading apparatus.

BRIEF DESCRIPTION OF THE DRAWINGS

Other objects and advantages of the present invention will become apparent upon reading the following detailed description and upon reference to the drawings in which.

DETAILED DESCRIPTION OF THE PREFERRED EMBODIMENT

Embodiments of the present invention will be described below. In this connection, the present invention is not limited to embodiments described below. Further, in the following description, although there is a description in which the meaning of the term is described, this is, to the utmost, the description of the meaning of the term in the embodiment, and the meaning of the term is not limited to this description.

Embodiment 1

Figure 1:
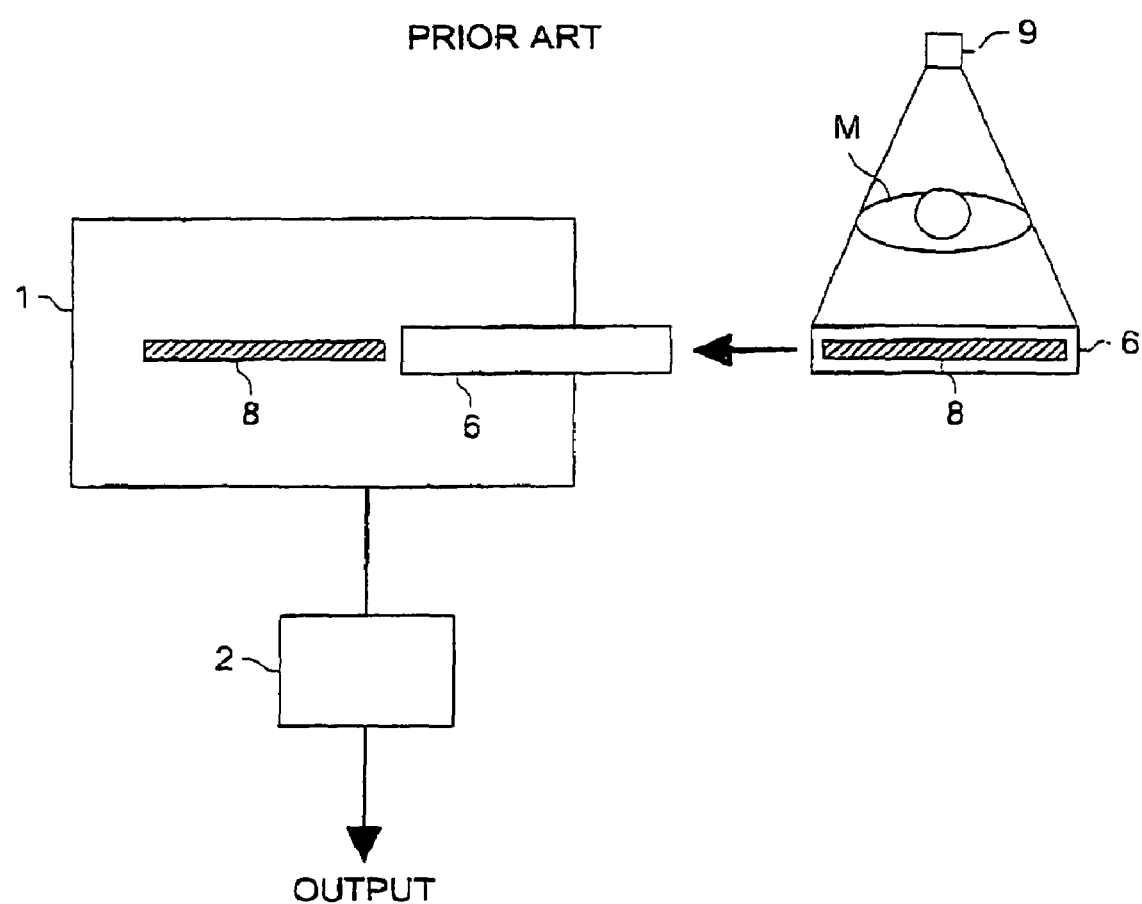
FIG. 1 is a view showing a structural example of the conventional cassette type radiation-image radiographing system.
Figure 2:
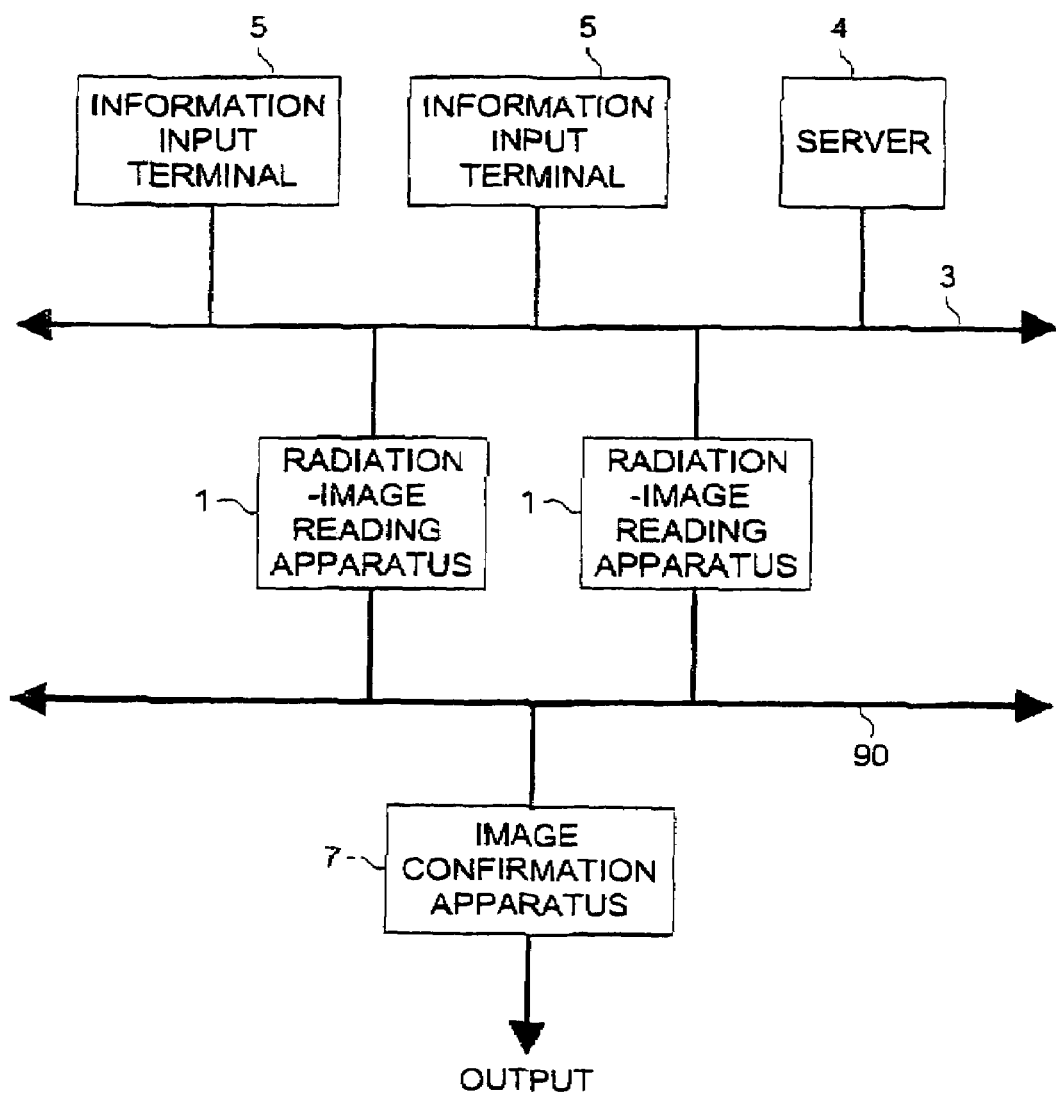
FIG. 2 is a view showing another structural example of the conventional cassette type radiation-image radiographing system.
Figure 3:
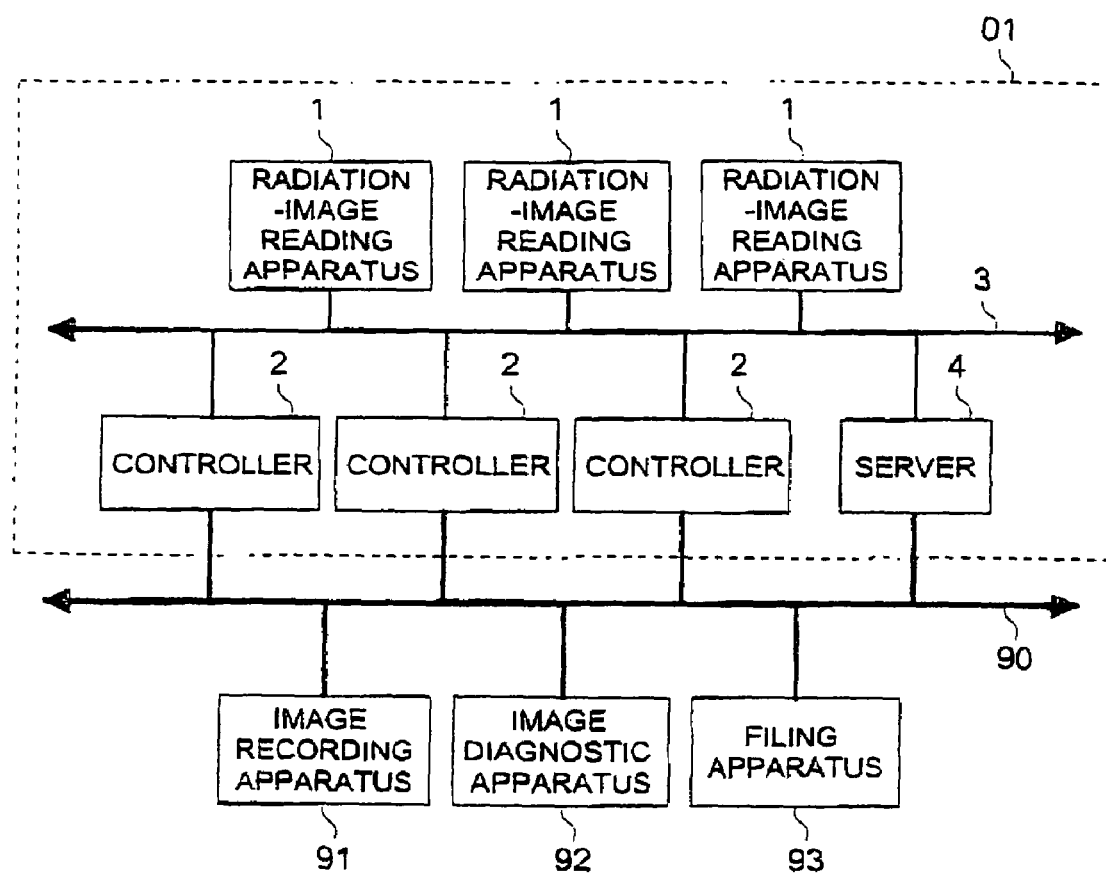
FIG. 3 is a view showing a structural example of a radiation-image radiographing system of an embodiment 1.

In a radiation-image radiographing system 01 of the present embodiment, as shown in FIG. 3, a plurality of radiation-image reading apparatus 1 and a plurality of controllers 2 and a server 4 are connected to each other through a network 3. The plurality of controllers are connected to a DICOM network 90. To the DICOM network 90, an image recording apparatus 91 such as a laser imager and an image diagnostic apparatus 92 and a filing apparatus 93 and so on can be connected. The image recording apparatus 91 provides the visualized diagnostic image to the doctor, by outputting the image data, which is outputted from the controller 2, on the film, and the image diagnostic apparatus 92 provides the visualized diagnostic image to the doctor by displaying the image data outputted from the controller 2 on a monitor. The image filing apparatus 93 stores the image data outputted from the controller 2. The image data stored in the image filing apparatus 93 can be outputted at need to the image output apparatus 91 or the image diagnostic apparatus 92.

Initially, referring to FIG. 4, the radiation-image radiographing system 01 of the present embodiment will be described below.

(1) On a casing of a cassette 6, a barcode 62 corresponding to an ID number (hereinafter, the ID number is called sheet ID number) to distinguish a stimulable phosphor substance sheet 8 housed in the cassette 6 is attached. Further, in the present embodiment, although it is structured such that the sheet ID number is distinguished by the barcode 62, for example, a non-contact ID label (S label) or an element called TIRIS (Texas Instrument) in which the code which is written in the element such as a label, can be read by using the wireless engineering using the electromagnetic wave, etc., may be used instead of the barcode 62.

When such the label whose code (sheet ID number) is read by using the wireless engineering is used, it is not necessary that the label is attached onto the casing of the cassette 6, and for example, the label may be attached onto the rear surface of the stimulable phosphor substance sheet 8. In this case, it is better when another label on which the ID number to distinguish the stimulable phosphor substance sheet 8 is written, is attached on the casing of the cassette 6.

The radiologist goes bringing with the cassette 6 to be used for the radiographing, to in front of the controller 2, and inputs the operator ID number at an operator ID number input section 23 of the controller 2. As this input section, the input device such as a finger print detector or a voiceprint detector which can distinguish the discrimination information based on the physical features of the operator own such as the finger print or voiceprint, or an ID card reader which reads the ID card, a barcode reader which reads the barcode label, or the input device such as a portable transmission signal receiver which receives the portable transmitter (because the ID card, barcode label, or portable transmitter can always be carried by the operator, it is convenient) is the optimum from the point of view of the accuracy of the information, and as the other methods, a key board or touch panel may also be used.

Further, an input section 22 which will be described later, may be structured so that it can commonly be used as the operator ID input section 23. Further, in order to neglect the troublesomeness of each time inputting, normally, in the case where one controller is used by one person, when the input is conducted once, it is convenient that this input is set as the default. Further, the ID number of the radiologist to be used is previously registered in the controller 2, and this may be selectable through a key board or touch panel.

Then, the radiologist registers the sheet ID number into the controller 2 such that the sheet ID is made to be read from the barcode 62 of the cassette 6 by using the barcode reader 24 of the controller 2, or the sheet ID is inputted from the input section 22 of the controller 2.

Further, the radiologist inputs the patient information of the patient to be photographed in this cassette 6 from the input section 22, and the radiographing information when the patient is photographed. Herein, the patient information is the name of the patient, age, sex, date of birth, and patient ID to specify the patient.

Further, the radiographing information is the information of the radiographing position (the information about which portion of the human body of the subject M) or radiographing method (the direction of the radiographing such as the rear front direction radiographing, front rear direction radiographing, side direction radiographing, or slanting position radiographing, or the information to specify the radiographing technique), and is not only used as the radiographing record of the patient, but also used as the image processing condition of the read-out image data, particularly the image processing parameter to determine the gradation conversion processing condition.

When the radiographing condition is determined, the system in which the reading condition such as the reading sensitivity or the reading resolving power (sampling pitch) of the radiation-image reading apparatus 1 is automatically selected, is provided.

In this connection, in the information, the re-usable information is stored as the default value as it is, and the input of the next time and after it may be simplified. Further, when the radiographing information or the patient information is previously registered, the structure in which the information is displayed as the list on the screen 21, and the radiologist selects the necessary information from the displayed list, may also be allowable.

The controller 2 makes the sheet ID number or operator ID number inputted from the barcode reader 24 or input section 22 correspond to a series of information such as the radiographing information or patient information, and reading condition, which are registered together with these ID numbers, (this series of information is called accompanied information), and temporarily stores them in the controller 2.

When there is an error in the sheet ID number, operator ID number, or accompanied information, displayed on the screen 21, the radiologist inputs the re-input instruction from the input section 22, and when information are correct, conducts the next input operation. Then, when these inputs are completed for all the cassettes to be photographed, the input to instruct the input completion is conducted. When the re-input instruction is inputted from the input section 22, the controller 2 clears the temporary memory such as the sheet ID number and waits the re-input.

Further, when the next sheet ID number is in putted, or the input completion is instructed, the temporarily stored sheet ID number and operator ID number and accompanied information are sent to the server 4 together with the ID number of the controller 2 (hereinafter, called controller ID number) and stored in the server 4. When the server 4 receives these information, the server 4 registers them in the radiographing data base as the record, serving as a recording file, accompanied by the photographed image proper ID number which is proper for each photographed image.

As described above, when the controller 2 registers the sheet ID number, the radiographing information corresponding to the cassette 6 is also registered together with it, and as will be described later, because the controller 2 image-processes and outputs the image data received together with the sheet ID number according to the photographic information coinciding with the sheet ID number, the registration mistake of the radiographing information due to the lapse of time as in the case where the radiographing information is registered after the image is read from the stimulable phosphor substance sheet 8 of the cassette 6, can be suppressed, and the correct image processing can be carried out.

Further, when the sheet ID number is registered by the controller 2, because the controller ID number is also registered together with the operator ID number corresponding to the cassette 6, these information can be utilized later. In this connection, the radiation-image reading apparatus 1 also has the ID number (apparatus ID number) to distinguish respective radiation-image reading apparatus 1.

(2) When a series of operations of the registration of each kind of ID numbers or the input of the accompanied information are completed, the radiologist positions the portion desired to be radioactive photographed of the subject M between the radioactive tube 9 and the cassette 6 (normally, the cassette 6 is brought into contact with the subject M), and operates the radioactive ray generation control apparatus 10 of the radioactive tube 9 and the radioactive ray is irradiated. Then, a part of the radioactive energy, which is irradiated from the radioactive tube 9 and transmitted through the subject M, is temporarily stored in the stimulable phosphor substance sheet 8 housed in the cassette 6.

(3) When the radiographing of the patient is completed, the assistant sets the cassette 6 for which the radiographing is completed, to the radiation-image reading apparatus 1. In this case, it is free to which radiation-image reading apparatus 1 the cassette 6 is set. Further, a plurality of cassettes 6 may be dispersedly set to a plurality of radiation-image reading apparatus 1.

When the cassette 6 is set, the radiation-image reading apparatus 1 reads the sheet ID number from the barcode 62 of the cassette 6, and searches the radiographing data base of the server 4 by this sheet ID number. The server 4 searches the radiographing data base by the sent sheet ID number, and the newest record in the coinciding records is obtained, and returns the information of the record to the radiation-image reading apparatus 1.

Then, the radiation-image reading apparatus 1 reads the radiation image information stored in the stimulable phosphor substance sheet 8 in the cassette 6 by the reading condition (reading sensitivity, or reading resolving power) described in the information of the returned record. That is, the excitation light is irradiated onto the stimulable phosphor substance sheet 8 and by the irradiated excitation light, the stimulation light emitted corresponding to the stored radiation image information is photoelectric converted, and the A/D converted digital image data (hereinafter, called image data, for simplification) is obtained. The obtained image data is transmitted to the controller 2 having the controller ID number returned from the server 4 together with the information of the record sent from the server 4.

When the reading of the image data is completed, the radiation-image reading apparatus deletes the energy remaining on the stimulable phosphor substance sheet 8, and returns the stimulable phosphor substance sheet 8 into the cassette 6, and the cassette 6 is made in a condition that it can be taken out. The assistant returns the cassette 6 to the radiographing room, and stands by the next radiographing.

As described above, in the embodiment of the present invention, the reading condition of the stimulable phosphor substance sheet 8 is automatically determined from the registered radiographing information, and because it is structured such that the determined reading condition is stored correspondingly to the sheet ID number, the radiation-image reading apparatus 1 searches the reading condition according to the read sheet ID number, and according to the obtained reading condition, the image data can be read from the stimulable phosphor substance sheet 8 of the cassette 6.

As described above, by only registering the radiographing information by the controller 2, because the image data can be read by the appropriate reading condition, the image data with the good image quality, which is optimal to the radiographing condition can be obtained.

(4) The radiologist conducts the confirmation operation of the received image data. Initially, while the controller 2 receives the image data from the radiation-image reading apparatus 1, the controller 2 forms the reduction image of the image data, and successively displays the reduction image on the screen 21. Further, the reduction image data is displayed together with the sheet ID number relating to the received image data or the apparatus ID number of the radiation-image reading apparatus 1 which transmits the image data, or the other accompanied information, on the screen 21. The content of these information displayed together with the image data (reduction image data) can be previously selected by the user.

When the reception of all the image data is completed, to the formed reduction image data, under the image processing condition determined by the radiographing information corresponding to the image data, the image processing such as non-linear gradation conversion processing is conducted, and displayed again on the screen 21. The radiologist confirms the image, which is displayed again, and when necessary, he can change the image processing condition, and conduct again the image processing to the reduction image data.

Further, the controller 2 notices the sheet ID number corresponding to the received image data to the server 4. The server 4 adds the information of the image transmission completion to the corresponding record in the radiographing data base by this notice. The controller 2 searches the temporarily stored information in the radiographing data base in the server 4 or the controller 2 by the patient ID number, and confirms whether all the image data of the sheet ID number having the corresponding patient ID number are returned to the controller 2. When all the image data of the sheet ID number having the corresponding patient ID number are returned to the controller 2, the information that all the image data of the corresponding patient are received, is displayed on the screen 21.

It is hardly judged whether the reading of all the cassette 6 relating to one patient is completed, from the operation condition of the radiation-image reading apparatus 1, however, when all the image read from the plurality of cassettes 6 relating to the one patient are received, because the controller 2 in which the sheet ID number is registered, displays that all of them are received, the operator can step to the next operation being satisfied.

Further, in the embodiment of the present invention, the display position of the image data or the output sequence can be re-arranged in a predetermined order. These may be automatically conducted or the operator may specify it. When it is desired to be automatically conducted, the re-arranged order is previously set. For example, when it is set to be re-arranged in the registration order of the sheet ID number, even when the input order of the cassettes 6 into the radiographing apparatus 1 is random, or reception order of the image data which is received by the controller 2 is random, because the display position of the image is always determined by the registration order, there is no confusion.

Further, in the embodiment of the present invention, even when the registration of the sheet ID number of the plurality of cassettes 6 for radiographing one patient is conducted by one controller 2, and the plurality of cassettes 6 which are photographed, are dispersedly set to the plurality of radiation-image reading apparatus 1, the images read by the plurality of radiation-image reading apparatus 1 are automatically returned to the controller 2 in which the sheet ID number is registered.

Therefore, even when it is the image data returned from the different radiation-image reading apparatus 1, the image data of the same patient can be collectively processed.

When the confirmation operation of the image is completed, the radiologist inputs the image determination. When the image determination is inputted, the image processing is conducted also on the image data which is not reduced, (received original image data) under the image processing condition which is finally conducted on the reduction image displayed on the screen 21, and the image processed image data is temporarily stored in the controller 2.

Then, the image processed image data or the image data before the image processing, added by the image processing condition, is transmitted to the image recording apparatus 91, image diagnostic apparatus 92, or image filing apparatus 93 according to the communication protocol of the DICOM, through the DICOM network 90, together with the other accompanied information or ID information. Further, when the image determination is inputted, a code showing the processing completion is added to the record relating to the corresponding sheet ID number of the radiographing data base in the server 4.

Figure 5:
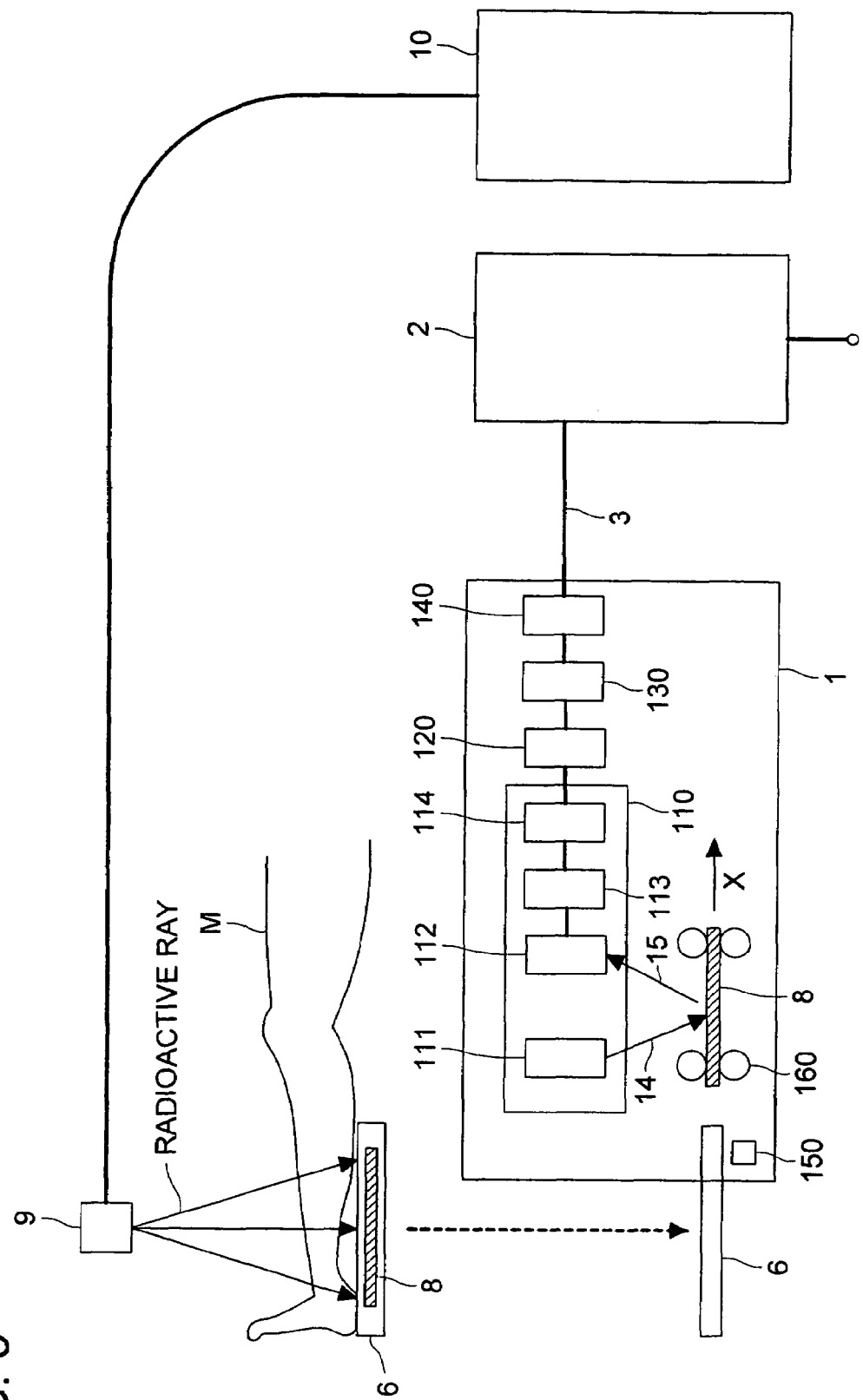
FIG. 5 is a view showing a radiation-image reading apparatus of the radiation-image radiographing system of the embodiment 1.
Figure 6:
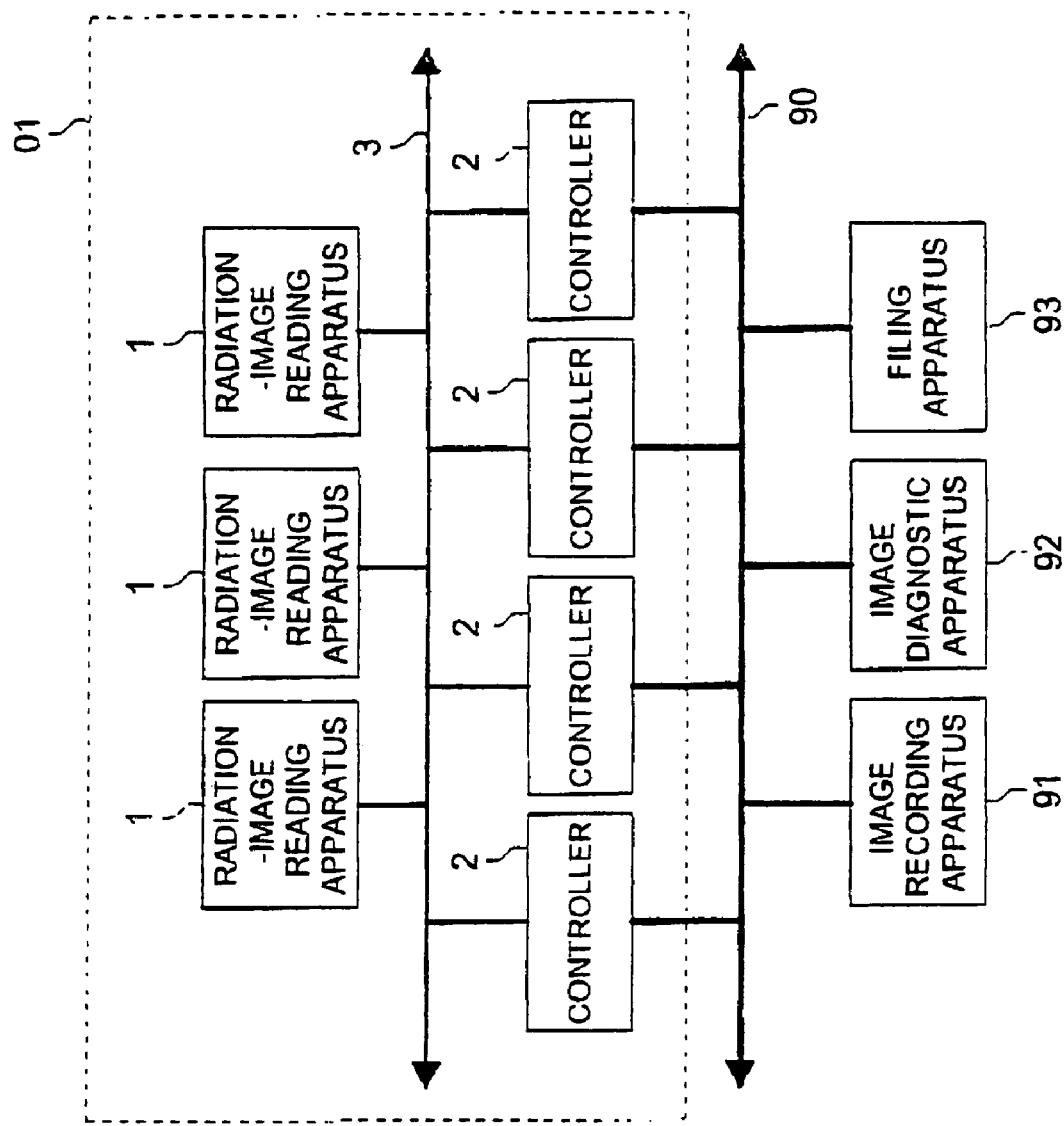
FIG. 6 is a view showing structural examples of the radiation-image radiographing systems of embodiments 2 and 3.

Next, referring to FIG. 5, the radiation-image reading apparatus 1 will be detailed.

After the completion of the radiographing, when the cassette 6 is set to the radiation image reading apparatus 1, the sheet ID number is read from the barcode 62 of the cassette 6 by a barcode reader 150. The searching of the server 4 is conducted by the sheet ID number, and as described above, the reading condition (reading sensitivity or reading resolving power) and the controller ID number of the image data return address is obtained. According to the value of the reading sensitivity, the sensitivity of the photoelectric reading section 112 is set, and according to the value of the reading resolving power, the conveying speed of a conveying mechanism 160 or the sampling pitch of an A/D converter 113 is set.

When the cassette 6 is set to the radiation image reading apparatus 1, the stimulable phosphor substance sheet 8 is pulled from the cassette 6, and while the stimulable phosphor substance sheet 8 is sub-scanning conveyed in the direction of X by the conveying mechanism 160, the image data stored and held in the stimulable phosphor substance sheet 8 is read out by the reading section 110.

The reading section 110 is composed of an excitation light generation section 111, photoelectric reading section 112, and A/D converter 113. While the stimulable phosphor substance sheet 8 is sub-scanning conveyed by the conveying mechanism 160, the excitation light generation section 111 irradiates the excitation light 14 for scanning in the direction perpendicular to the sub-scanning direction (main-scanning direction).

When the excitation light 14 acts upon the stimulable phosphor substance sheet 8, because the energy stored inside the fluorescent substance is generated as the stimulation light 15, the stimulation light 15 is collected, and converted into the electric signal by the photoelectric reading section 112, and the electric signal is logarithmically converted by a logarithmic converter 114 (thereby, the electric signal is converted from the electric signal which is linear to the light intensity of the stimulation light 15, into the electric signal which is logarithmically linear to the light intensity of the stimulation light 15, that is, the electric signal which is linear to the density), and further, it is digitized by the A/D converter 113.

The correction processing proper to the reading section 110 or the stimulable phosphor substance sheet 8 (the shading correction of the photoelectric reading section 112, the unevenness correction due to the excitation light generating section 111, the sensitivity unevenness correction of the stimulable phosphor substance sheet 8 and so on) is conducted on the image data outputted from the reading section 110 in the signal processing section 120, and after that, the processed data is successively, temporarily stored in the temporary storing section 130. Then, after the reading is completed, (or while the image data is read out), the communication section 140 transmits the image data to the controller 2 having the controller ID number which is returned from the server 4, through the network 3.

The image data transmitted to the controller 2 is the image data having the pixel value which is linear to the logarithm of the light intensity of the stimulation light 15, and which is improper to the diagnosis in the gradation characteristic as it is (in many cases, it can not be used for the diagnosis). In order to convert it to the image data, which can be used for the diagnosis, it is necessary that, generally, the non-linear gradation conversion processing is conducted, however, in the present embodiment, this processing is conducted in the controller 2. As described above, in the present embodiment, while the gradation characteristic, which is improper to the diagnosis, remains as it is, the image data is returned from the radiation-image reading apparatus 1 to the controller 2.

Because the processing condition of the non-linear gradation conversion processing is different depending on the radiographing position or the radiographing direction, it is necessary that the algorithm is prepared for each radiographing position or radiographing direction. Further, on the other hands, because the algorithm to automatically detect the irradiation field diaphragm of the radioactive ray at the radiographing or the subject area is necessary, the algorithm of the non-linear gradation conversion processing has generally very complicated structure.

Because the cost of the circumstances in which such complicated image processing algorithm is carried out at high speed, (called image processing circumstance), is very high, it is very uneconomical to structure the image processing circumstance on both of the radiation-image reading apparatus 1 and the controller 2. In the present embodiment, because the circumstances in which the radiologist confirms the image and then, changes the image processing condition, and under the changed image processing condition, the image processing is conducted again, is provided, the image processing circumstances are necessary on the controller 2 side. Accordingly, it is better to structure the system in such a manner that, on the radiation-image reading apparatus 1 side, the image processing is not conducted, and the image processing is conducted only on the controller 2 side.

However, even when it is structured such that the image processing can be conducted on the radiation-image reading apparatus 1 side, the essence of the present invention excluding the cost is not spoiled.

Figure 4:
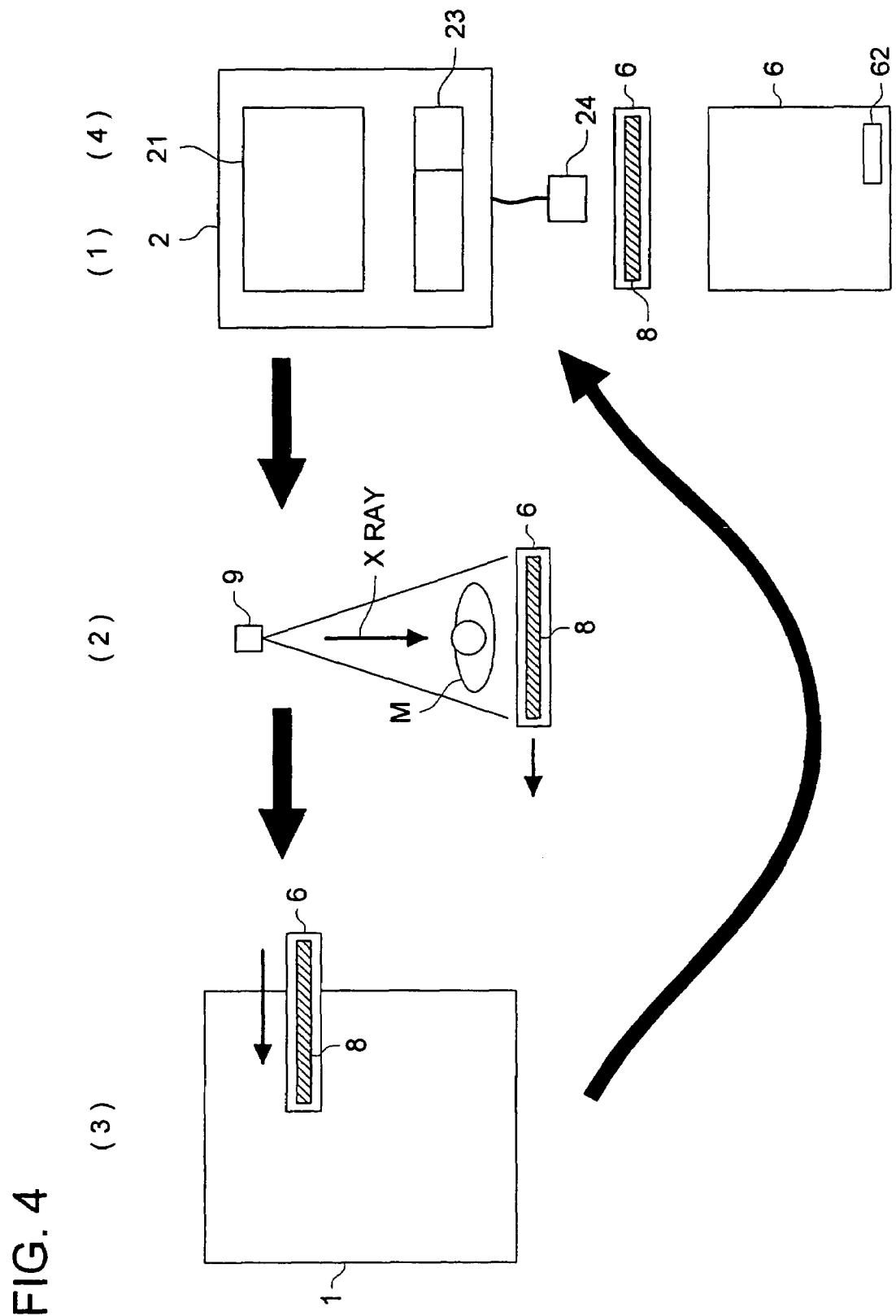
FIG. 4 is a view showing motions of the radiation-image radiographing system of the embodiment 1.

Next, referring to FIG. 4, the controller 2 will be further detailed. The controller 2 has the display section 21 to display the various information or the read images, the input section 22 for the radiologist to input the instructions, the operator ID input section 23 to input the ID of the operator such as the radiologist, and the barcode reader 24 to read the barcode 62 of the cassette 6. Further, the controller 2 is connected to the server 4 and a plurality of radiation-image reading apparatus 1 through the network 3. Further, the controller 2 can also be connected to the image recording apparatus 91, image diagnostic apparatus 92, or image filing apparatus 93 through the DICOM network 90.

As the input section 22, the key board, touch panel, or voice input apparatus can be used, but, it is not limited to them.

Further, the controller 2 or server 4 can connect to the hospital information system (HIS) or the radioactive information system (RIS). In this case, it is preferable that the patient information or the radiographing information is taken in on-line from these HIS or RIS. Further, it may be allowable that the patient is made to have a portable memory medium in which the above-described information is stored, and the memory medium reading apparatus is provided in the controller 2, and the information such as the patient information or the radiographing information is read from the potable memory medium which is brought by the patient. As such the portable memory medium and the memory medium reading apparatus, the barcode and the barcode reader, or the magnetic card and the magnetic card reader, or the IC card and the IC card reader can be listed, but, it is not limited to them.

Further, for the patient ID number, the coinciding data may be searched from the HIS, or RIS. In this case, the patient is made to have a portable memory medium in which the patient ID number is stored, and the memory medium reading apparatus is provided, and these information may be read from the portable memory medium which is brought by the patient, but, it is not limited to this, the information may be inputted from the input section 22, or the information proper to the patient such as the finger print or voice print is stored in the HIS or RIS, and the finger print detecting apparatus or voice print detecting apparatus is provided in the controller 2, thereby, by the detected finger print or voice print, the coinciding data may be searched from the HIS or RIS.

Further, as the display section 21 of the controller 2, when it is a means by which the character information or the image information can be displayed, such as the CRT display or liquid crystal display, it may be good, and as the content to be displayed, the apparatus ID number to specify the radiation-image reading apparatus 1 which obtained the image data, operator ID number, patient information, radiographing information, reading condition, radiographing condition (for example, the tube voltage of the radioactive tube, or radiation dose) obtained from the radiation generation control apparatus 10 of the radiation tube 9, information such as the number of pixels or matrix size, number of bits per 1 pixel of the image data, kind of the image processing, image processing parameter, or content of the correction processing, and the image of the photographed image data, are listed, but it is not limited to them.

Further, it may also be allowable that the radiographing position is selected by 2 steps of the rough large classification based on the main component of the human body, and further fine small classification. As an example of the large classification in this case, for example, [the head], [the chest], [the abdomen], [the upper limbs], [the lower limbs], [the backbone], [the basin]. Further, the small classification is the classification in which the position shown by the large classification is further finely classified, and for example, when the large classification is [the upper limbs], the small classification is [humeral joint], [shoulder blade], [humerus], [elbow joint], [forearm born], [hand joint], [carpus], and [finger born]. Further, the radiographing direction is generally, the radiographing direction to the human body, but, it is not limited to that.

As the typical example of such the radiographing direction, [PA: Posteroanterior Projection], [AP: Anteroposterrior Projection], [LAT: lateral radiography], and [Oblique Radiography] are listed.

Further, as the kind of the image processing conducted by the controller 2, the gradation conversion processing to convert the gradation of the image data, frequency processing to convert the frequency characteristic of the image data, or dynamic range compression processing to compress the dynamic range of the image data is listed, but, it is not limited to them.

Specially, in the present embodiment, because the system is structured such that the image data having the pixel value which is linear to the logarithm of the light intensity of the stimulation light is transmitted from the radiation-image reading apparatus 1 to the controller 2, it is absolutely necessary that the non-linear gradation conversion processing can be conducted by the controller 2.

As described in the above, according to the abovementioned embodiment, one of cassettes 6 can be dispersedly loaded into an arbitral one of radiation-image reading apparatus 1, irrespective of the controller 2, which registers the sheet ID number of the cassette concerned. In addition, the image data read by said arbitral one of radiation-image reading apparatus 1 is automatically returned to the controller 2, in which the sheet ID number of the stimulable phosphor substance sheet 8 corresponding to said image data is registered.

As described above, because the cassette whose sheet ID number is registered by one controller 2 can be set to any one of a plurality radiation-image reading apparatus 1, the low cost radiation-image reading apparatus 1 in which the number of cassettes 6 which can be set to the apparatus is small, can be used. Thereby, the installation area of the apparatus can be reduced, the introduction cost can be lowered, and the expandability can be further increased.

Further, because the cassette 6 whose sheet ID number is registered by one controller 2 can be simultaneously read out by the plurality of radiation-image reading apparatus 1, in the hospital in which many radiographing can be carried out one time for one patient, the processing ability of the radiation-image radiographing system can be increased.

Further, when m sets of radiation-image reading apparatus 1 in each of which n sheets of cassettes can be set are connected with each other, because maximum n×m cassettes can be continuously set, when large number of cassettes are desired to be processed once, there is no troublesomeness for the set of the cassettes, and the radiographing cycle time can be very reduced.

Further, when m radiation-image reading apparatus 1 are connected, because maximum m radiation-image reading apparatus 1 can simultaneously read the image data, as compared to the case where one radiation-image reading apparatus 1 reads the image data, the reading-out time is reduced to 1/m (the processing ability is increased to m times). Accordingly, also for the hospital in which many radiographing are carried out once for one patient, or the radiographing cycle is short, the ideal operation circumstance which is effective and in which there is no delay of operation, can be provided.

Further, even when a plurality of radiation-image reading apparatus 1 are used per one patient, because one controller 2 can input the patient information or accompanied information such as the radiographing condition, the input operation becomes effective.

Further, even when a plurality of radiation-image reading apparatus 1 are used per one patient, because the image data is collected in the one controller 2 in which the patient information of this patient or radiographing information is registered (that is, the sheet ID number of the stimulable phosphor substance sheet 8 used for the radiographing of this patient is registered), it is not necessary that the radiologist moves between the terminal equipment for registration of the patient information of the patient or radiographing information and the terminal equipment for the image confirmation, thereby, the operation efficiency can be increased. Further, because the registration of the patient information of the patient or radiographing information and the image confirmation can be conducted by one controller 2, the correspondence relationship between the registered information and the image data can be confirmed, thereby, the reliability of the operation can be increased.

Further, because there are a plurality of controllers 2, the controller 2 can be installed at a position near the site of the radiographing, and the radiologist can conduct the input of the patient information or radiographing information, or the confirmation of the image or selection of the image processing condition at the position near the site of the radiographing, thereby, the circumstance in which the operation efficiency is good, and the operation can be easily conducted, can be provided.

Further, even when the radiation image radiographing apparatus 1 of a portion of the plurality of radiation-image reading apparatus 1 is faulty, because the other no-faulty radiation image radiographing apparatus 1 can cope with that, the reliable system can be structured.

Further, because the server 4 collectively controls the radiographing data base, its information can be referred later, and the radiographing history can be controlled without fail.

Next, in the present embodiment, when the radiation image read from the stimulable phosphor substance sheet 8 of the cassette 6 by the radiation-image reading apparatus 1, is tried to be transmitted to the specified controller 2, the case where it can not be transmitted to the controller 2, will be described.

Such the case occurs due to, for example, the connection failure of the terminal of the network, runaway of the CPU due to the bug in the program or the heat generation, or malfunction or failure of the component such as the hard disk drive. Further, when it is tried to be transmitted to the specified controller 2, whether it can not be transmitted to the controller 2, can be detected by detecting that communications can not be established.

Further, when an alarm device which emits alarm by the control from the radiation-image reading apparatus 1 or server 4, or displays the alarm is provided, or when a means for detecting the communication fault is provided in the controller 2 and the communication fault is displayed, it is noticed to the radiologist that the using controller 2 has the communication fault.

As the resolving means when the communication fault is detected, the following 6 solutions are considered. These may be appropriately selected according to the convenience of the hospital side. The first solution is to specify the controller 2 of the transmission destination of the image data from the other controller 2. This method includes further 3 solutions described below.

1) This solution is a method in which the user selects the other controller 2, and directly sends the controller ID number of the return address to the radiation-image reading apparatus 1 holding the image data desired to receive, and requires the return of the image data.

The radiation-image reading apparatus 1 which receives the request transmits all the image data, which is held by the apparatus 1, to the controller 2 having the specified controller ID number. The merit of this solution is that the control mode of both of the controller 2 side and the radiation-image reading apparatus 1 side is simplest, and the development cost of the control software is low, and the system can be easily operated stably.

2) This solution is the method in which the user selects the other controller 2, and registers the operator ID number by the selected controller 2, and sends the operator ID number and the controller ID number of the return address to all of the radiation-image reading apparatus 1, and requires the return of the image data having the transmitted operator ID number.

When the radiation-image reading apparatus 1 which receives this request holds the image data having the required operator ID number, the image data having the required operator ID number is transmitted to the controller 2 having the specified controller ID number.

3) This solution is the method in which the user selects the other controller 2, and registers the operator ID number by this selected controller 2, sends the operator ID number and the controller ID number of the return address to the server 4, and requires the return of the image data having the transmitted operator ID number.

When the system is set in such a manner that the radiation-image reading apparatus 1 whose communication is not established, always searches the server 4, at the time point when the server 4 receives the request, the radiation-image reading apparatus 1 can take in this request. The radiation-image reading apparatus 1 which takes in this request transmits the image data having the required operator ID number to the controller 2 having the specified controller ID number.

The merit of the above-described 2) and 3) is: by using the operator ID number, the other controller 2 can receive the image data which is desired to be received by the user, selectively and simply. Because the image data is received by using the operator ID number as a key word, the possibility that the image data to be received by the other controller, is received by mistake, can be avoided.

The second solution is the method in which the radiation-image reading apparatus 1 compulsively transmits the image data together with the additional information showing the secondary distribution data to all the other controllers 2 which are not faulty.

The controller 2 which received the image data and additional information temporarily saves the received image data and additional information, and when they become unnecessary, the controller 2 deletes them. For example, when the user selects the other controller 2, the determination declaration that the temporarily saved image data and the additional information are its own data and information, is conducted. When this determination declaration is transmitted to the other controllers 2, the other controllers 2 can delete the temporarily saved image data and additional information.

For example, the operator ID number may also be used for the declaration method of this determination declaration. In this case, the operator ID number in which the sheet ID number is registered is included in the additional information sent by the radiation-image reading apparatus 1. Then, when the user selects the other controller 2, the operator ID number is registered by the selected controller 2. The controller 2 compares the newly registered operator ID number with the operator ID number in the temporarily saved additional information, and when these coincide with each other, the controller 2 considers that the determination declaration is conducted.

The merit of this solution is that, when the user selects the other controller 2, because the image data is already received, (because the provability that the image data is received, is high), the image confirmation can be conducted at once by the arbitrary controller 2.

The third solution is that the image save function is provided in the server 4, and the radiation-image reading apparatus 1 transmits the image data to the server 4 as a substitute of the transmission of the image data to the specified controller 2, and the server 4 temporarily saves the transmitted image data.

When the user selects the other controller 2 and the transmission of the temporarily saved image data is required from the selected controller 2 to the server 4, the temporarily saved image data is transmitted from the server 4 to the controller 2, which has required.

For example, in the case where the transmission of the temporarily saved image data is required from the controller 2 to the server 4, when the operator ID number is used, it is convenient. That is, when the user selects the other controller 2, the operator ID number is registered by the selected controller 2. Then, when the transmission of the temporarily saved image data is required to the server 4, the operator ID number is also sent to the server 4. The server 4 finds out the image data having the same ID number as the sent operator ID number from the temporarily saved image data, and returns it to the controller 2.

The merit of this solution is that, because the transmission destination of the image data from the radiation-image reading apparatus 1 is always fixed to the server, the development of the control software on the radiation-image reading apparatus 1 side is simple, and the development cost is low, and by simple control, the system is stably moved. Further, because the image data is searched by making the operator ID number the key word, the possibility that the image data which is tried to be received by the other controller is received by mistake, can be avoided.

The fourth solution is the method in which, when the transmission to the controller 2 to which the image data is to be originally transmitted, can not be conducted, the order of the controller 2 to be transmitted is previously determined, and according to the order, the transmission of the image data is conducted to the next ordered controller 2. In this case, when the controller 2 has the communication fault, it is preferable that the user previously knows the controller 2 to be transmitted.

The merit of this solution is that, even when the user conducts nothing, the image data is automatically transmitted to the predetermined another controller 2. The fifth solution is the method in which a function which can specify the controller 2 to transmit the image data is provided in the radiation-image reading apparatus 1, and the user uses this function and specifies the controller 2 to return the image data when the user specifies the controller 2 which can be communicated, the image data is transmitted to the controller 2. Further, when the system is structured in such a manner that a plurality of controllers 2 or servers 4 can be simultaneously specified, it is further convenient.

The merit of this solution is that the control mode of both of the controller 2 side and the radiation-image reading apparatus 1 side is simple, and the development cost of the control software is low, and further, it is easily moved stably. Further, because the plurality of controllers 2 and servers 4 can be specified as the transmission destination, the system with the high safety can be structured.

The sixth solution is the method in which the writing apparatus of the portable memory medium is also provided in all of radiation-image reading apparatus 1, and further, in all of controllers 2, the reading apparatus of this portable memory medium is provided, and the image data which can not be returned is stored in the portable memory medium, and the portable memory medium is set in the other controller 2 and the image data is transferred into the controller 2.

As such the portable memory means, photo-magnetic disk, magnetic disk, optical disk, memory card, and portable hard disk drive are listed, but, it is not limited to them.

The merit of this solution is that, even when whole of the network 3 has the communication fault, the system can cope with it.

As described above, in the present embodiment, even when the image data read out by the radiation-image reading apparatus 1 can not be transmitted to the specified controller 2, because the image data can be transmitted to another controller 2, even when the controller of a portion in a plurality of controllers 2 has the fault during its use, another controller 2 can cope with it, and the system which is easily used and reliable can be provided.

Further, except for the fourth solution, there is a merit that the radiologist can select the controller 2 corresponding to the using condition of a plurality of controllers 2 when the communication fault is generated.

Further, when the specified controller 2 commonly has the function of the server 4, even when the server 4 is faulty, because all the record of the radiographing data base is saved in the controller 2, there is no trouble for the radiographing operation. It is further preferable when all of the controller 2 commonly have the function of the server 4.

Next, in the case of emergency, the case in which, leaving the registration relating to the patient or radiographing till later on, it is desired that the reading out of the radiation image is conducted first, will be described.

(1) The radiologist positions a portion which is desired to be radioactive photographed, of the subject M between the radioactive tube 9 and the cassette 6, and operates the radiation generation control apparatus 10 of the radioactive tube 9 and irradiates the radiation. Then, a portion of the radiation energy which is irradiated from the radioactive tube 9 and penetrated the subject M is stored once in the stimulable phosphor substance sheet 8 housed in the cassette 6.

(2) When the radiographing of the patient is completed, the assistant sets the cassette 6 to which the radiographing is completed, in the radiation-image reading apparatus 1. When the cassette 6 is set to the radiation-image reading apparatus 1, the apparatus 1 reads the sheet ID number from the barcode 62 of the cassette 6, and the radiographing data base of the server 4 is searched by this sheet ID number.

The server 4 searches the radiographing data base by the sent sheet ID number, but the newest record can not be obtained in the coincided records. Accordingly, it returns the answer that there is no coincided record, to the radiation-image reading apparatus 1. The radiation-image reading apparatus 1 reads out the image data under the default reading condition, and the read out image data is temporarily stored in the radiation-image reading apparatus 1.

Next, it is desired that the controller 2 to transmit the image is specified, but it is unknown to which controller 2 the image may be transmitted. In this case, it can be solved by the similar solutions as the case of the above-described communication fault. These solutions may be appropriately selected corresponding to the convenience of the hospital.

The first solution is the method in which the controller 2 of the transmission destination is specified from the controller 2 side. That is, from the controller 2, the controller ID number of the return address is directly sent to the radiation-image reading apparatus 1 holding the image data, which is desired to be received, and the return of the image data is required.

The radiation-image reading apparatus 1 received this request transmits all the holding image data together with the additional information such as the read sheet ID number, and reading condition, to the controller 2 having the specified controller ID number.

The merit of this solution is that the control mode of both of the controller 2 side and the radiation-image reading apparatus 1 side is simplest, and the development cost of the control software is low, and further, the system can be easily moved stably.

The second solution is the method in which the radiation-image reading apparatus 1 compulsively transmits the image data together with the additional information such as the information showing the after registration data, or the read out sheet ID number, and read out condition, to all the controller 2. The controller 2 which receives the image data and the additional information temporarily saves the received image data and the additional information, and when they become unnecessary, they are deleted.

For example, when the user selects another controller 2, the determination declaration to determine that the temporarily saved image data and the additional information are its own data and information, is conducted. When this determination declaration is transmitted to the other controllers 2, the other controllers 2 can delete the temporarily saved image data and the additional information.

The merit of this solution is that, when the user selects the other controller 2, because the image data is already received (because the provability that it is received is high), the image confirmation can be made at once by the arbitrary controller 2.

The third solution is the method in which the image save function is provided to the server 4, and the radiation-image reading apparatus 1 transmits the image data together with the additional information such as the information showing the after registration data, read out sheet ID number, and reading out condition, and the server 4 temporarily saves the transmitted image data and the additional information.

When the user requires the transmission of the temporarily saved after registration image data from the controller 2 to the server 4, the temporarily saved image data and its additional information is transmitted from the server 4 to the controller 2.

The merit of this solution is that, because the transmission destination of the image data from the radiation-image reading apparatus 1 is always fixed to the server, the development of the control software on the radiation-image reading apparatus 1 side is simple, the development cost is low, and the system can be stably moved by the simple control.

The fourth solution is the method in which the order of the controller 2 which transmits in the case of the after registration data is previously determined, and according to the order, the image data is transmitted to the controller 2 together with the additional information such as the information showing the after registration data, read out sheet ID number, and read out condition. In this case, it is preferable that the user previously knows the controller 2 to be transmitted in the case of the after registration data.

The merit of this solution is that, the image data is automatically transmitted to the predetermined another controller 2 without the user operating anything.

The fifth solution is the method in which a function which can specify the controller 2 to return the image data is provided in the radiation-image reading apparatus 1, and the user uses the function and specifies the controller 2 to which the image data is returned. When the user specifies the controller 2, the image data is transmitted to the controller 2 together with the additional information such as the information showing the after registration data, read out sheet ID number, and read out condition. Further, it is further convenient when the system is structured such that a plurality of controllers 2 or servers 4 can be simultaneously specified.

The merit of this solution is that the control mode of both of the controller side and the radiation-image reading apparatus 1 side is simple, and the development cost of the control software is low, and further, the system can be easily moved stably. Further, because the a plurality of controllers 2 and servers 3 can be specified as the transmission destination, the system with the high safety can be structured.

The sixth solution is the method in which the writing apparatus of the portable memory medium is provided in any radiation-image reading apparatus 1, and further, the reading apparatus of this portable memory medium is provided in any controller 2, and the image data is stored in the potable memory medium together with the additional information such as the sheet ID number which is read out the image data, and the reading condition, and the potable memory medium is set to the desired controller 2, and the image data and the additional information are transferred to the controller 2.

The merit of this solution is that, even when the whole the network 3 has the communication fault, the system can cope with it. As described above, in the case of emergency, even when, leaving the registration relating to the patient and the radiographing till later on, the reading out is conducted first, the transmission of the read out image data can be conducted to the controller 2.

(3) The radiologist inputs the patient information when the radiographing is conducted by the cassette 6, and additional information such as the radiographing information from the input section 22 of the controller 2. When the patient information or the radiographing information is determined, the controller 2 conducts the image processing under the image processing condition determined according to the radiographing information on the received image data, and displays the image processed image data on the screen 21. After that, the radiologist can change the image processing condition at need. When the change of the image processing condition is inputted, the controller 2 image processes the image data under the changed image processing condition, and displays on the screen 21 again. The controller 2 temporarily stores the inputted patient information or accompanied information such as the radiographing information, or operator ID number together with the reading condition.

When there is an error in the information displayed on the image screen 21, the radiologist can correct it by inputting the re-input instruction from the input section 22. Then, when these inputs relating to all the received image data are completed, the input instructing the input completion is conducted.

When a series of processing or input operation is completed and the image data or accompanied information is determined, the temporarily stored sheet ID number, operator ID number, reading condition, or accompanied information is transmitted together with the ID number of the controller 2 (hereinafter, called controller ID number) to the server 4.

The server 4 adds the radiographing image proper ID number for each radiographing image to the received sheet ID number, operator ID number, reading condition, or accompanied information, and registers this record in its radiographing data base.

Embodiment 2

The embodiment 2 is a modified embodiment of the embodiment 1, and is an embodiment in which the function of the server 4 of the embodiment 1 is not used (even when there is no server, the system can be operated). The points at which embodiment 2 are different from embodiment 1 will be detailed in the following. In addition, the same descriptions as those for embodiment 1 will be omitted in the following.

According to embodiment 2, the sheet ID number or reading condition (reading sensitivity or reading resolving power) is registered by the controller 2, and these are determined, then, these information including at least sheet ID number are transmitted together with the controller ID number (normally, controller ID number of the controller 2 in which the sheet ID number or reading condition is registered) of the controller 2 of the return address, to all or predetermined specified radiation-image reading apparatus 1. In other words, before the cassette 6 in which the sheet ID number is registered is set to any of the radiation-image reading apparatus 1, the transmission of the image data is previously required to a plurality of radiation-image reading apparatus 1.

In the present embodiment, the image data transmission request notice in which the information such as the sheet ID number, reading condition, and controller ID number of the return address is written is formed, and this image data transmission request notice is transmitted to all of the radiation-image reading apparatus 1.

The radiation-image reading apparatus 1 received the image data transmission request notice temporarily stores the received image data transmission request notice.

At an arbitrary timing, the cassette 6 is set to the radiation-image reading apparatus 1, and when the sheet ID number is read from the barcode 62 of the cassette 6, the apparatus 1 searches whether the same sheet ID number as the sheet ID number read from the barcode 62 by the radiation-image reading apparatus 1 exists in all of the image data transmission request notice temporarily stored in the radiation-image reading apparatus 1. When the coincided sheet ID number is detected, the controller ID number of the return address is obtained from the image data transmission request notice, and it is noticed to the controller 2 having this controller ID number that the cassette 6 having the desired sheet ID number is detected.

In the present embodiment, the ID detection notice in which the detected sheet ID number and its own apparatus ID number are written is formed, and this ID detection notice is transmitted to the controller 2 of the return address.

Further, the radiation-image reading apparatus 1 reads the image data from the stimulative fluorescent substance sheet 8 included in the cassette, according to the reading condition specified in the corresponding image data transmission request notice, and transmits the read out image data to the controller 2 of the return address.

When the coincided sheet ID number can not be discovered, the same countermeasure as in the above described [in the case of the emergency, the case where, leaving the registration relating to the patient or radiographing till later on, the reading is conducted first] may be taken.

When the controller 2 receives the ID detection notice, it is temporarily stored in the controller 2, and checks the sheet ID number written in the received ID detection notice, and confirms that, to which image data transmission request notice, the corresponding sheet ID number is detected.

Next, the request to cancel the image data transmission request notice corresponding to the detected sheet ID number is transmitted to the radiation-image reading apparatus 1 from which at least the ID detection notice is transmitted. In the present embodiment, the cancellation request notice in which the detected sheet ID number is written, is transmitted to all of the radiation-image reading apparatus 1 from which the ID detection notice is not transmitted.

The radiation-image reading apparatus 1 received the cancellation request notice searches the image data transmission request notice having the same sheet ID number as the sheet ID number described in the cancellation request notice in all of temporarily stored image data transmission request notice, and cancels (erase) this.

The timing at which the controller 2 transmits the cancellation request notice to the radiation-image reading apparatus 1, may be before the image data is received, or after it. In this connection, the system is structured in such a manner that, when the sheet ID number corresponding to the image data transmission request notice is detected in the radiation-image reading apparatus 1, the ID detection notice is transmitted from the radiation-image reading apparatus 1 to the controller 2, and when the controller 2 receives this, and transmits the cancellation request notice to the radiation-image reading apparatus 1 from which at least the ID detection notice is not transmitted, the image data transmission request notice which becomes unnecessary, is cancelled, but, by using the other means, the image data transmission request notice which becomes unnecessary, may be cancelled.

For example, the request to cancel the image data transmission request notice having the detected sheet ID number may be noticed from the radiation-image reading apparatus 1 which detected the sheet ID number to the other radiation-image reading apparatus 1.

Embodiment 3

The embodiment 3 is a modified embodiment of the embodiment 2. The points at which embodiment 3 are different from embodiment 2 will be detailed in the following. In addition, the same descriptions as those for embodiment 2 will be omitted in the following.

According to embodiment 3, when the sheet ID number or reading condition (reading sensitivity, or reading resolving power) is registered by the controller 2, these information are temporarily stored in the controller 2. However, different from the embodiment 2, the controller 2 does not transmit the image data transmission request notice in which the information such as sheet ID number, reading condition, and controller ID of the return address, is written, to the radiation-image reading apparatus 1 at this point.

When the cassette 6 is set to the radiation-image reading apparatus 1 and the sheet ID number is read from the barcode 62 of the cassette 6, at least read sheet ID number and its own apparatus ID are noticed to all of the controllers 2. In the present embodiment, the ID detection notice in which the read sheet ID and its own apparatus ID number are written is formed, and this ID detection notice is transmitted to all of the controllers 2.

Further, when the controller 2 receives the ID detection notice, this is temporarily stored in the controller 2, and the controller 2 searches whether the same sheet ID number as the sheet ID number written in the ID detection notice exists in the information temporarily stored in the controller 2. When the corresponding sheet ID number is detected, the transmission of the image data is required to the radiation-image reading apparatus 1 from which the ID detection notice is transmitted.

In the present embodiment, the controller 2 forms the image data transmission request notice in which the information such as the sheet ID number, reading condition, and controller ID of the return address is written, and transmits it to the radiation-image reading apparatus 1 from which the ID detection notice is transmitted.

When the corresponding sheet ID number can not be discovered in the information temporarily stored in the controller 2, the same countermeasure as in the above described [in the case of the emergency, the case where, leaving the registration relating to the patient or radiographing till later on, the reading is conducted first] may be taken.

Next, the request to cancel the image data transmission request notice corresponding to the detected sheet ID number is transmitted to the radiation-image reading apparatus 1 from which at least the ID detection notice is transmitted. In the present embodiment, the cancellation request notice in which the detected sheet ID number is written, is transmitted to all of the radiation-image reading apparatus 1 from which the ID detection notice is not transmitted.

The radiation-image reading apparatus 1 received the cancellation request notice searches the image data transmission request notice having the same sheet ID number as the sheet ID number described in the cancellation request notice in all of temporarily stored image data transmission request notice, and cancels (erase) this.

When the radiation-image reading apparatus 1 receives the image data transmission request notice, the image data is read from the stimulable phosphor substance sheet 8 included in the cassette 6 according to the reading condition specified in this packet, and the read out image data is transmitted to the controller 2 specified by the controller ID number of the return address in the image data transmission request notice.

The timing at which the controller 2 transmits the cancellation request notice to the radiation-image reading apparatus 1, may be before the image data is received or after it.

As described above in the embodiments 2 and 3, in the mode in which the function of the server 4 is not used, the radiation-image radiographing system by which the same effect as in the embodiment 1 can be obtained, can be structured.

Further, also in the embodiments 2 and 3, when the radiation image which is read from the stimulable phosphor substance sheet 8 of the cassette 6 by the radiation-image reading apparatus 1 is tried to be transmitted to the specified controller 2, there is a case where the transmission to the controller 2 can not be conducted. In this case, in the solutions as described in the embodiment 1, by the solution in which the server 4 is not used, this problem can be avoided.

Further, also in the embodiments 2 and 3, there is a case where, in the case of emergency, leaving the registration relating to the patient or radiographing till later on, it is desired that the reading of the radiation image is conducted first. In this case also, in the solutions as described in the embodiment 1, by the solution in which the server 4 or the operator ID number is not used, this problem can be avoided.

Further, in the present embodiment, even a cassette 6 whose sheet ID number is registered by any controller 2, because it can be dispersedly set to arbitrary radiation-image reading apparatus 1, and the function to realize that the image data read out by the arbitrary radiation-image reading apparatus 1 is automatically returned to the controller 2 in which the sheet ID number of the stimulable phosphor substance sheet 8 corresponding to the image data is registered, is provided in respective controller 2 and the radiation-image reading apparatus 1, thereby, this function can be realized not though the specified server 4, accordingly, when the function of the server 4 is broken down, there is no possibility that the whole system does not function. Further, even when any controller 2 or radiation-image reading apparatus 1 has the fault, the automatic return function of the image data is not lost.

Relating to the above-described 3 embodiments of the present invention, the further modified embodiment will be described below.

Figure 7:
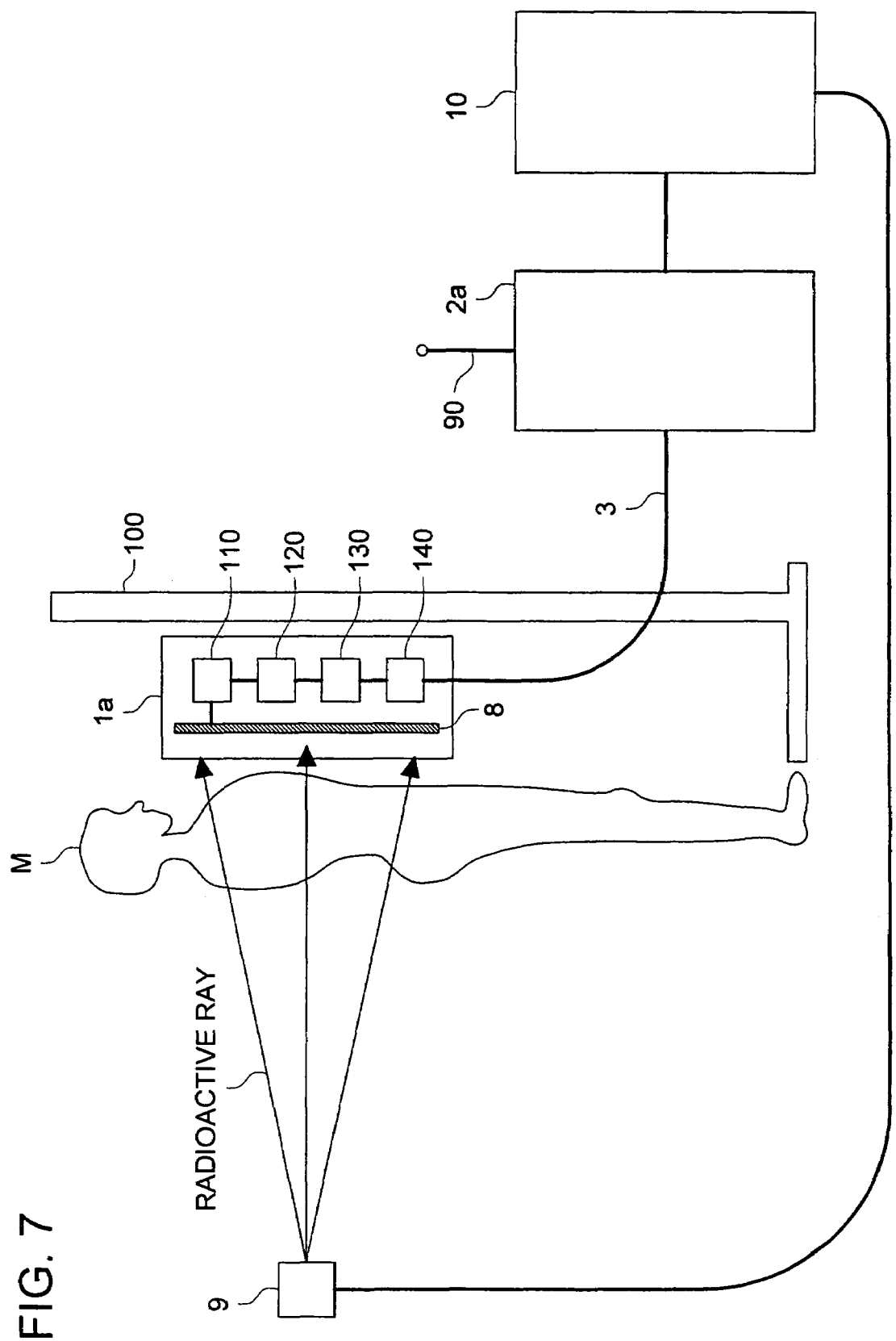
FIG. 7 is a view showing a structural example of an exclusive (standing type) radiation-image radiographing system.
Figure 8:
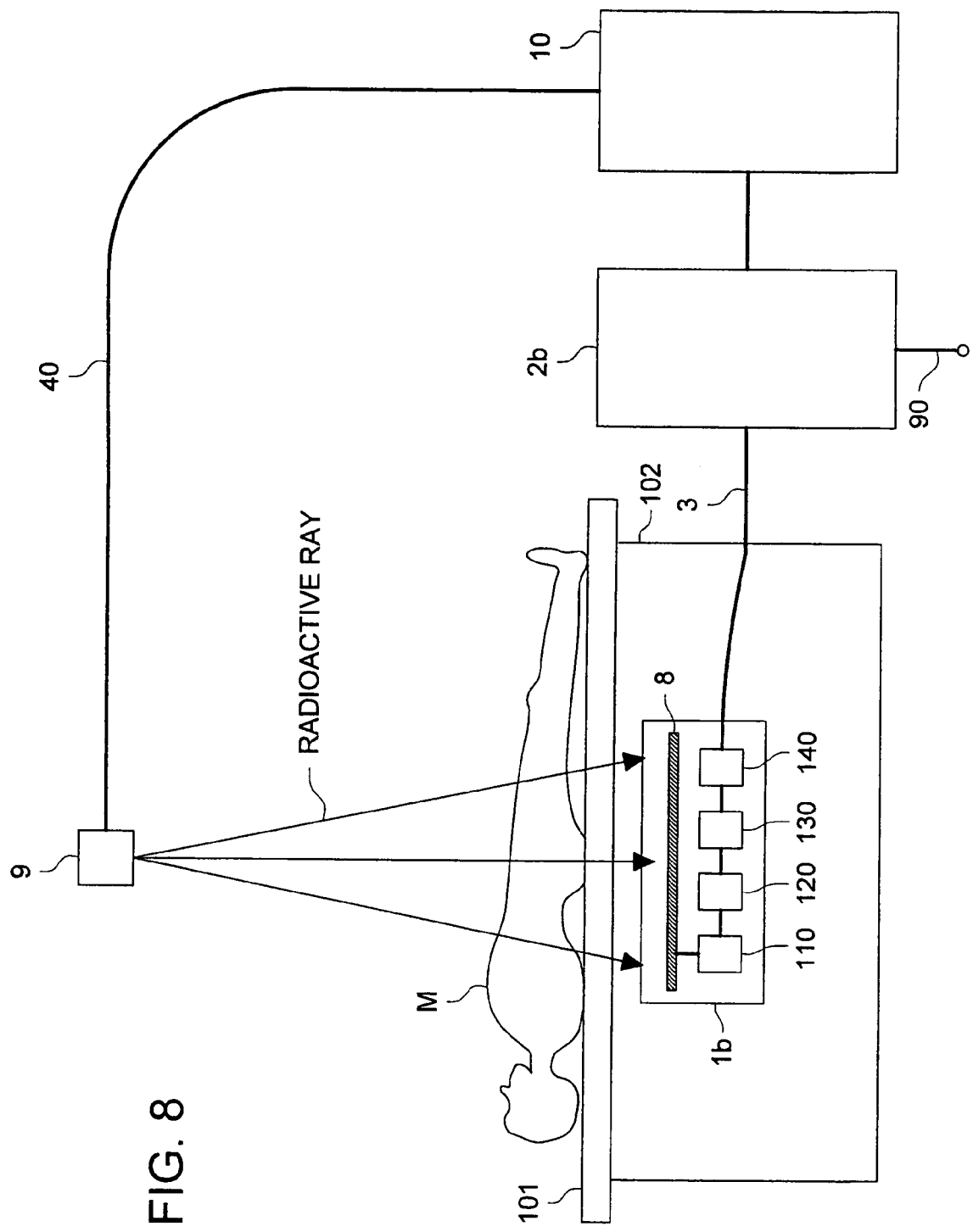
FIG. 8 is a view showing a structural example of an exclusive (lying type) radiation-image radiographing system.

Generally, in the radiation-image reading apparatus, besides the radiation-image reading apparatus 1 using the cassette 6 as shown in FIG. 5, (hereinafter, this type radiation-image reading apparatus is appropriately called the cassette type radiation-image reading apparatus), there are exclusive type radiation-image reading apparatus as shown in FIG. 7 and FIG. 8. The exclusive type radiation-image reading apparatus is the radiation-image reading apparatus in which the user can not simply carry the detection means because the detection means (detector section) detecting the X ray is fixed inside the radiographing apparatus or housed there. As the detection means, besides the stimulable phosphor substance sheet 8, the solid plane detector can also be used.

FIG. 7 is a view showing a standing type radiation-image reading apparatus 1a, and the apparatus 1a is structured by a ramp 100 and the radiation-image reading apparatus 1a.

FIG. 8 is a view showing a laying type radiation-image reading apparatus 1b, and the apparatus 1b is structured by a plate-like member 101, bed 102, and radiation-image reading apparatus 1b.

The radiation-image reading apparatus 1a and the radiation-image reading apparatus 1b are respectively structured by a reading section 110, signal processing section 120, primary storing section 130, and communication section 140, and both of the function and movement are the same as the radiation-image reading apparatus 1 described in FIG. 5. Further, the inside of the reading section 110 is structured by the excitation light generating section, photoelectric reading section, and A/D converter (any one of them is not shown), and both of the function and movement are the same as the radiation-image reading apparatus 1 described in FIG. 5.

The different points of the radiation-image reading apparatus 1a and the radiation-image reading apparatus 1b from the radiation-image reading apparatus 1 are following 3 points.

1) The reading out of the stimulable phosphor substance sheet 8 is started synchronized with the generation of the radiation from the radiation tube 9.

2) For having this synchronization, the controller 2a, 2b conducts the communication relating to the synchronous signal of the radiation irradiation with the radiation generation control apparatus 10.

The registration of the sheet ID number of the stimulable phosphor substance sheet 8 is not necessary.

Next, the movement in the case where the radiation-image reading apparatus 1a and the radiation-image reading apparatus 1b are used will be described.

After the radiologist registers the patient by the controller 2a, 2b, he sets the subject M at a predetermine position of the radiation-image reading apparatus 1a or the radiation-image reading apparatus 1b, and operates the radiation generation control apparatus 10 of the radiation tube 9 and irradiates the radiation. Then, a portion of the X ray energy which is irradiated from the X ray tube 9 and penetrated the subject M is stored once in the stimulable phosphor substance sheet 8 housed in the cassette 6.

Being synchronized with this radiation irradiation, the reading section 110 reads the image information from the stimulable phosphor substance sheet 8, and through the signal processing section 120, primary storing section 130, and communication section 140, the image data is transmitted to the controller 2a or 2b.

Till now, these exclusive type radiation-image reading apparatus and the cassette type radiation-image reading apparatus are controlled by individual controllers. However, when the exclusive type radiation-image reading apparatus and the cassette type radiation-image reading apparatus are arranged in the same radiographing room, because it is necessary that they are controlled by respectively different controllers, the disadvantage that the number of installations of the controller, installation area, installation cost are increased, is indicated. Further, when the same patient is photographed by the exclusive type radiation-image reading apparatus and the cassette type radiation-image reading apparatus, because it is necessary that the registration of the patient information and radiographing information, and the image confirmation are conducted by different controller, thereby, the operation efficiency is very lowered, and the operation mistake is increased.

In the embodiment of the present invention, in order to solve these problems, the exclusive type radiation-image reading apparatus 1a and 1b can be controlled by the cassette type controller 2.

Figure 9:
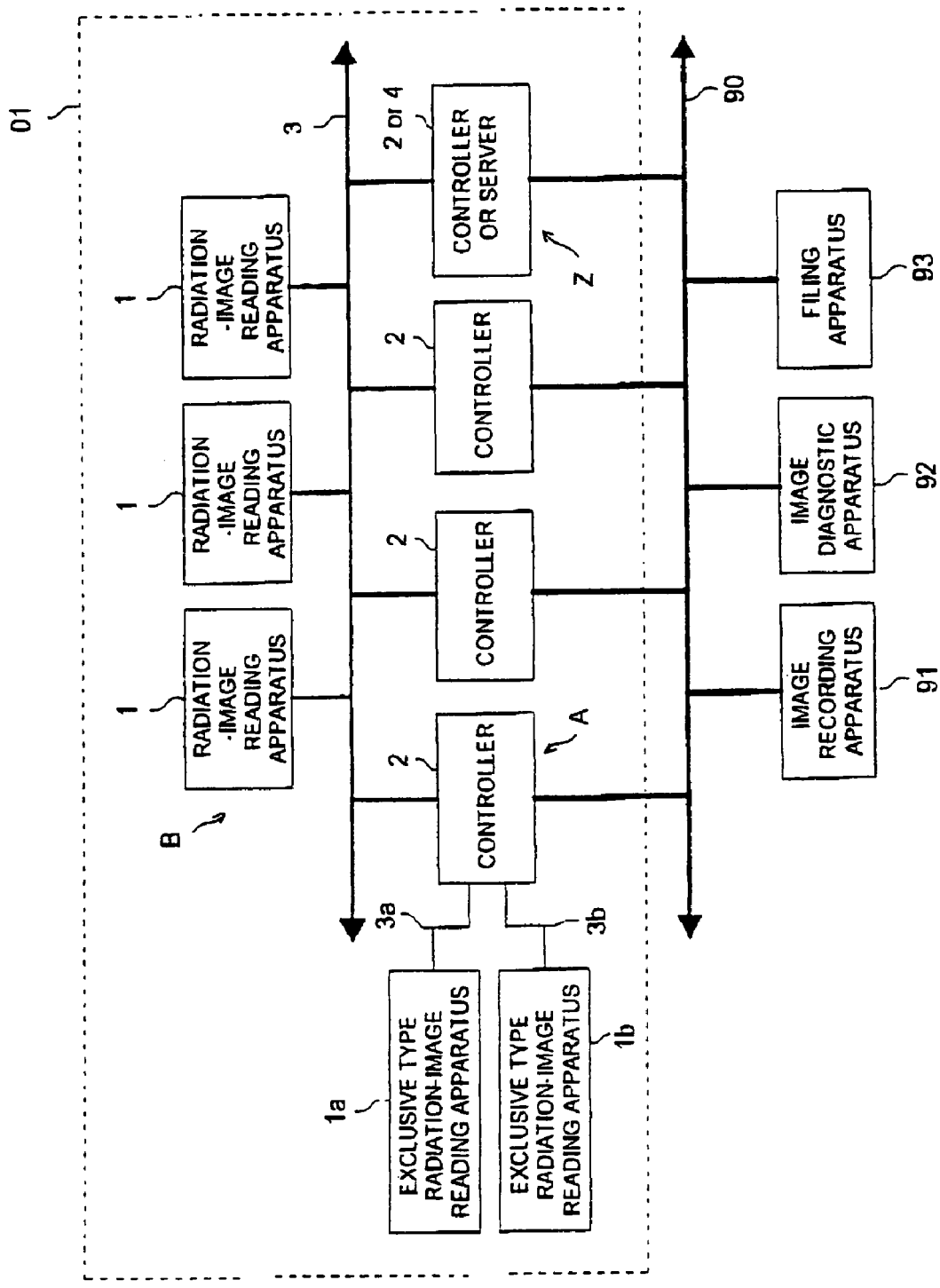
FIG. 9 is a view showing a structural example of the radiation-image radiographing system, which is a modified mode of the embodiment 1.

FIG. 9 is a view showing an example of this embodiment and the modified example of the embodiments 1, 2 and 3. The exclusive type radiation-image reading apparatus 1a and 1b are connected to the controller 2 shown by an arrow A, respectively through private lines 3a and 3b. The other controller 2 can also connect the exclusive type radiation-image reading apparatus 1a and 1b in the same manner. In the present embodiment, the case is assumed that exclusive type radiation-image reading apparatus 1a and 1b, and the cassette type radiation-image reading apparatus shown by an arrow B, are installed in the same radiographing room, and the radiologist normally uses these radiation-image reading apparatus by the controller 2 shown by the arrow A.

In this case, because the exclusive type radiation-image reading apparatus 1a and 1b are connected to the controller 2 shown by the arrow A through the private lines 3a and 3b, the image data transmitted from the exclusive type radiation-image reading apparatus 1a and 1b can be received only by the controller 2 shown by the arrow A. However, the controller 2 shown by the arrow A can receive the image data from not only the cassette type radiation-image reading apparatus 1 shown by the arrow B, but also from the other cassette type radiation-image reading apparatus 1.

Thereby, when the exclusive type radiation-image reading apparatus and the cassette type radiation-image reading apparatus are installed in the same radiographing room, it is not necessary that respectively different controllers control the apparatus, thereby, the number of installations of the controllers, installation area, and apparatus cost can be lowered. Further, when the same patient is photographed by the exclusive type radiation-image reading apparatus and the cassette type radiation-image reading apparatus, because the registration of the patient information, and radiographing information or the image confirmation can be conducted by the same controller, the operation efficiency is increased and the operation mistake can be reduced.

Figure 10:
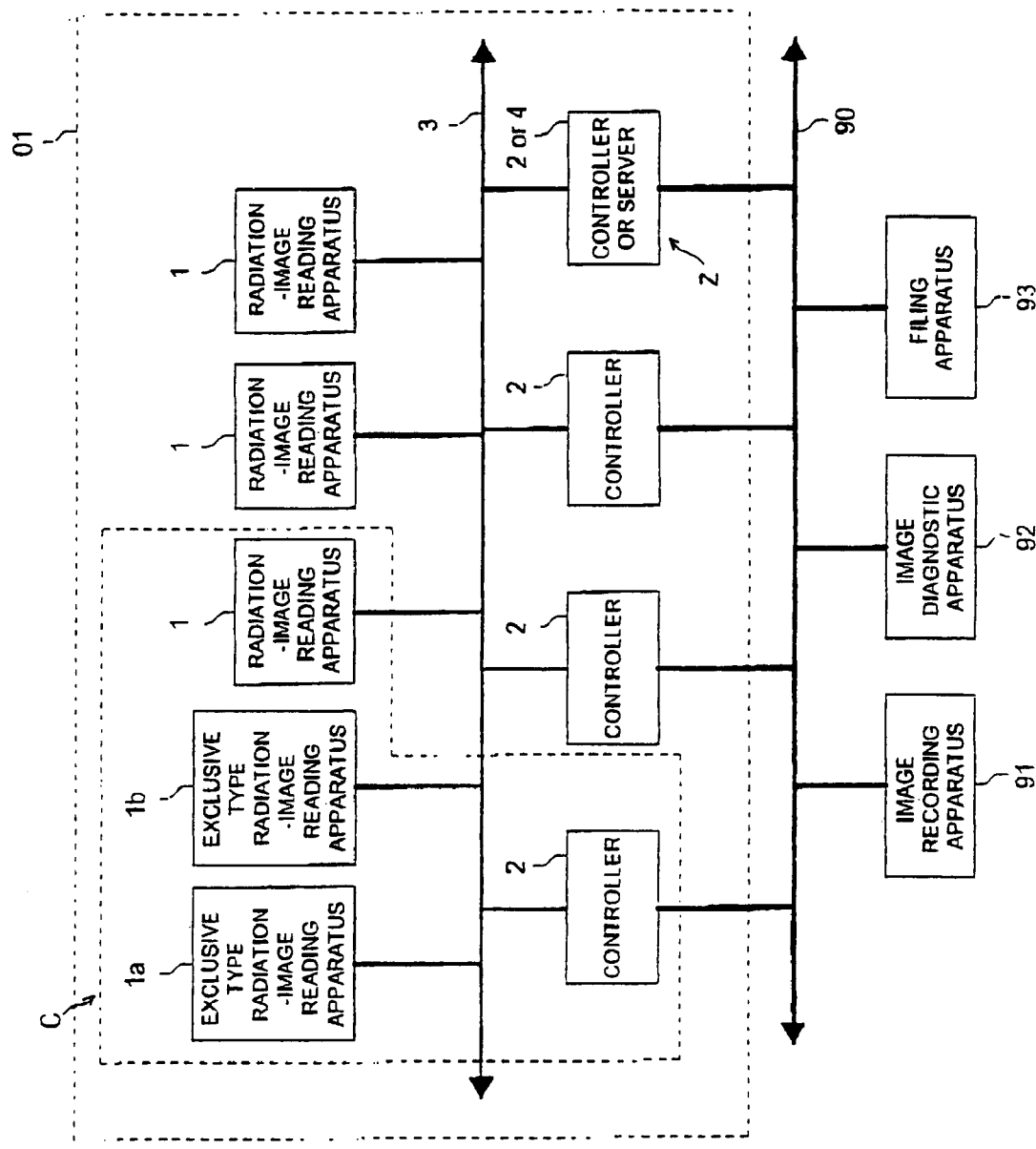
FIG. 10 is a view showing a structural example of the radiation-image radiographing system, which is a modified mode of the embodiment shown in FIG. 9.

FIG. 10 is a modified embodiment of the embodiment in FIG. 9, and the exclusive type radiation-image reading apparatus 1a and 1b are connected to arbitrary controllers 2 through network 3. Therefore, the arbitrary controller 2 can receive the image data from the exclusive type radiation-image reading apparatus 1a and 1b. A case in which the apparatus surrounded by dotted line shown by an arrow C are installed in one radiographing room, is assumed in FIG. 10.

When the exclusive type radiation-image reading apparatus 1a and 1b are used, the radiologist normally conducts the registration of the patient information and radiographing information, or image confirmation by the controller 2 shown by an arrow D, however, by any trouble, when the controller 2 shown by the arrow C can not receive the image data transmitted from the radiation-image reading apparatus 1a and 1b, the image data can be received by the other controller. Accordingly, the high reliable system can be structured.

Figure 11:
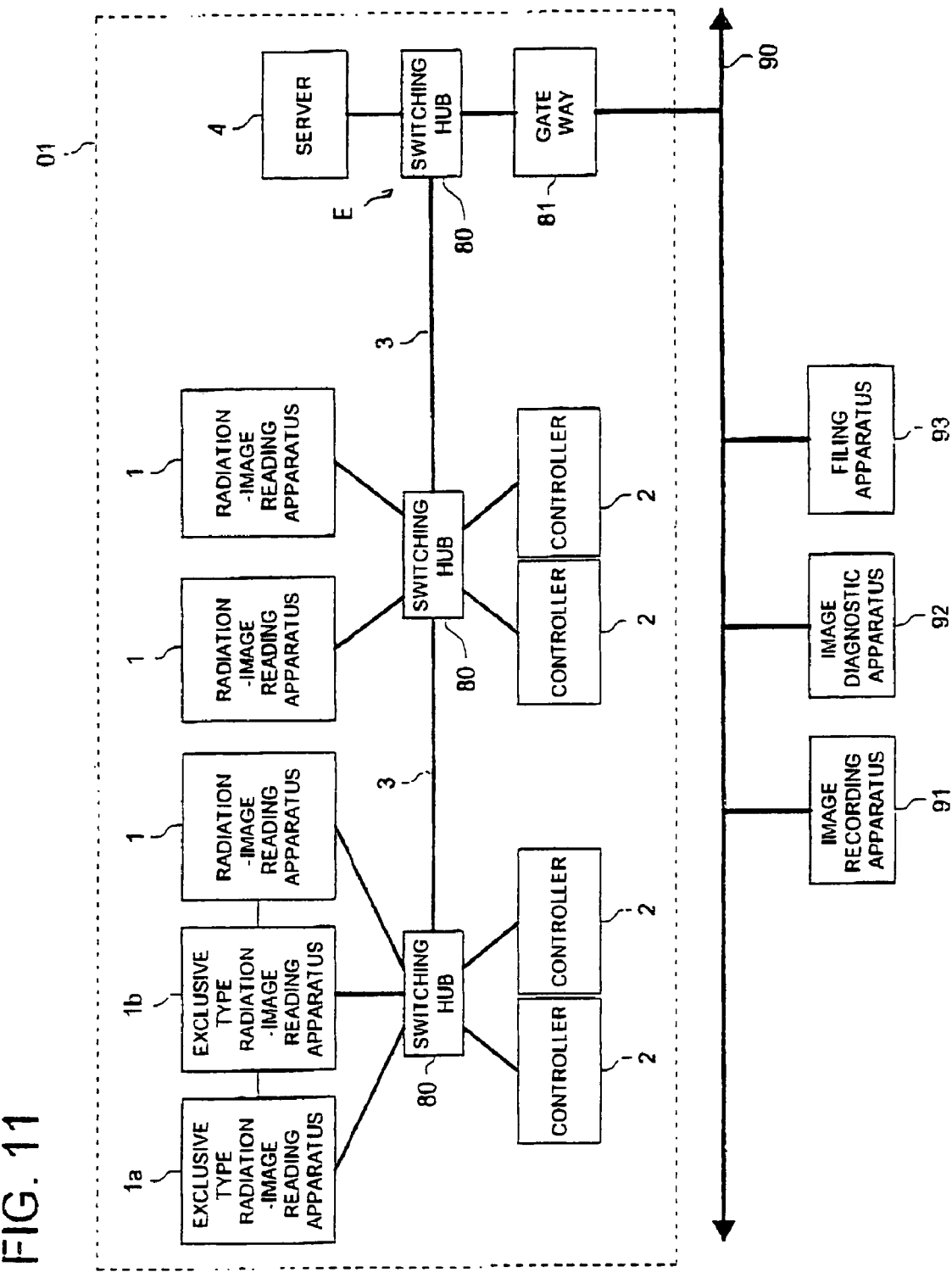
FIG. 11 is a view showing a structural example of the radiation-image radiographing system, which is a modified mode of the embodiment shown in FIG. 10.

FIG. 11 is a modified example of the embodiment of FIG. 10, and the exclusive type radiation-image reading apparatus 1a and 1b and the cassette type radiation-image reading apparatus 1 or controllers 2 are connected by a switching hub 80. The server 4 is connected to the switching hub shown by an arrow E, however, even when the server 4 does not exist, it is needless to say that the system can be operated without any problem as in the embodiments described above.

The network 3 and the DICOM network 90 are connected by a gate way 81. The image data outputted by the controller 2 is outputted to the DICOM network 90 through the switching hub 80 and the gate way 81. In this embodiment, because the exclusive type radiation-image reading apparatus 1a and 1b or cassette type radiation-image reading apparatus 1, or controller 2 are dispersedly connected by the switching hub 80, the image data transmission time when the image data transmission between the exclusive type radiation-image reading apparatus 1a and 1b and the controller 2 is generated at the same time, is improved. Because a large quantity of image data flow on the network 3 connecting between switching hubs 80, it is preferable that the cable with large transmission capacity is used.

Figure 12:
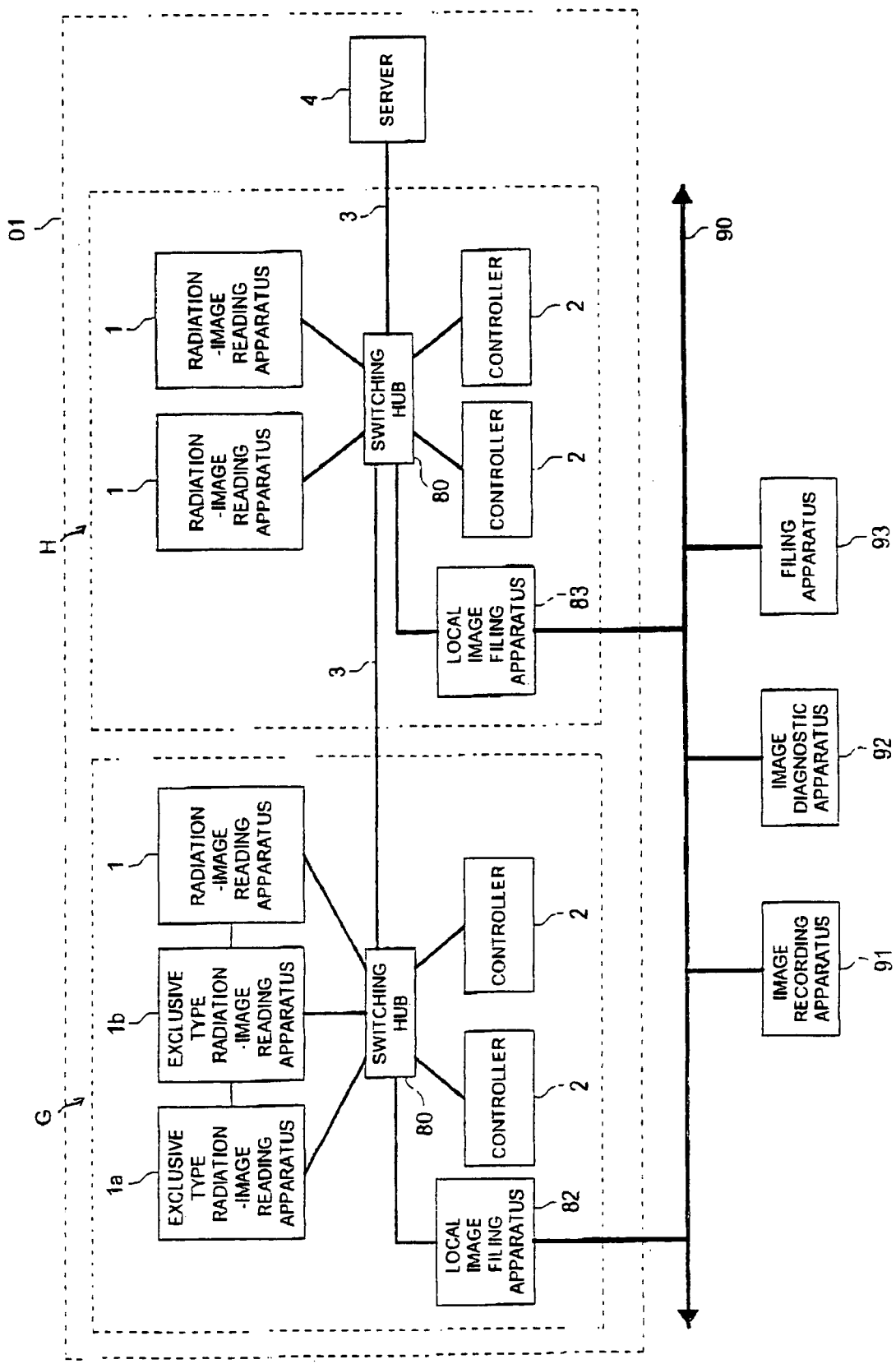
FIG. 12 is a view showing a structural example of the radiation-image radiographing system, which is a modified mode of the embodiment shown in FIG. 11.

FIG. 12 is a modified embodiment of the embodiment of FIG. 11. Local image filing apparatus 82 and 83 commonly used as the DICOM gate way, file the image data generated in portions respectively surrounded by arrows G and H. The server 4 is a server which controls the information generated in portions surrounded by dotted lines of arrows G and H, and even when this server 4 does not exist, it is needless to say that the system can be operated without any problem as in the embodiments described above. The data base in the local image filing apparatus 82 and 83 are controlled by the image filing apparatus 93.

The image recording apparatus 91 described in the embodiment 1, image diagnosis apparatus 92 or image filing apparatus 93 can be connected to the DICOM network 90 in FIG. 9, FIG. 10, FIG. 11, and FIG. 12.

According to the present invention, even a cassette whose discrimination information is registered any controller of the plurality of controllers, or even when the cassette is set to any radiation-image reading apparatus, because any controller can register the discrimination information, and any radiation-image reading apparatus, can read the discrimination information of the radiation-image storing sheet, the registered information can corresponds to the read out image.

Because the radiation-image storing sheet in which the discrimination information is registered by one controller, can be set to any one of the plurality of radiation-image reading apparatus, the number of the radiation-image storing sheets which can be set per one radiation-image reading apparatus, cab be reduced, thereby it can be structured at comparatively low cost.

Because a plurality of cassette can be dispersedly set to the plurality of reading apparatus, the operation efficiency is increased, and because the plurality of radiation-image image reading apparatus parallely read the image data, the processing ability is increased, and further, there are a plurality of controllers, the controller can be installed at a near position of the site of the radiography, and the radiologist can conduct the input of the patient information and radiographing information relating to the radiography and reading or image confirmation, or change of the image processing at the position near the site of the radiographing, and the circumstance in which the operation efficiency is good and the operation can be easily conducted, can be provided.

Further, the installation area of the apparatus is reduced and the introduction cost can be made to low cost, and further, the expandability becomes high, and further, even when some of radiation image reading apparatus in the plurality of radiation-image reading apparatus is faulty, because the other radiation image radiographing apparatus which is not faulty, can cope with even a radiation image storing sheet body in which the discrimination number is registered by any controller, it is a system which can be easily operated and in which the reliability is high.

According to the present invention, in addition to the effect of the invention of the cited item, further, even when some of the controller in a plurality of the controllers is faulty during the using time, because the other controllers can cope with it, it is a system which can be easily operated and in which the reliability is high.

According to the present invention, in addition to the effect of the invention of the cited item, further, even when some of the controller in a plurality of the controllers is faulty during the using time, because the controller operated by the operator who registered the discrimination information of the radiation-image storing sheet, in the other controllers, copes with it, even when the controller is faulty during the using time, it is a system which can be easily operated and in which the reliability is high.

According to the present invention, in addition to the effect of the invention of the cited item, further, when a plurality of radiation-image storing sheets relating to one subject are dispersedly set to the plurality of radiation-image reading apparatus, it is hardly judged from the operating condition of the radiation-image reading apparatus whether the read out of all the radiation-image storing sheet relating to the one subject is completed, however, because, when the controller by which the registration of the discrimination information of plurality of radiation-image storing sheets relating to the one subject receives all of the image read from the plurality of radiation-image storing sheets relating to the one subject, it conducts any display, the operator can steps to the next operation without anxiety.

According to the present invention, in addition to the effect of the invention of the cited item, further, when a plurality of radiation-image storing sheets relating to one subject are dispersedly set to the plurality of radiation-image reading apparatus, the image transmitted from the radiation-image reading apparatus is returned in the different radiographing order according to the operation condition of the plurality of radiation-image reading apparatus at that time points, or in the order without any relationship with the set order of the cassette, however, because the images read from the plurality of radiation-image storing sheets relating to one subject can be re-arranged in a predetermined order and outputted, the images can be outputted in a predetermined order.

According to the present invention, in addition to the effect of the invention of the cited item, further, in order to establish the communication means among the plurality of radiation-image reading apparatus and the plurality of controllers, because the information exchange may be conducted only to the specified server having the data base means, the control means is simplified, and the system can be stably moved. Further, because the data base means can collectively control the various information relating to radiographing, this information can be referred later, and the radiographing history can be controlled correctly.

According to the present invention, in addition to the effect of the invention of the cited item, further, because the record including the discrimination information of the radiation-image storing sheet registered by the controller and the discrimination information of the controller is saved in all of the radiation-image reading apparatus, there is no case where the system can not cope with it at all as in the case where the server has a fault when the record is saved only in the specified server, and the image data can be surely returned to the controller.

According to the present invention, in addition to the effect of the invention of the cited item, further, because the discrimination number of the radiation-image storing sheet read out by the radiation-image reading apparatus is directly inquired to each controller, there is no case where the system can not cope with it at all, as in the case where the server has a fault when the record is saved only in the specified server, and the image data can be surely returned to the controller.

According to the present invention, in addition to the effect of the invention of the cited item, further, because the reading can be conducted under the appropriate reading condition registered by the controller, the image data having the high image quality can be obtained.

According to the present invention, in addition to the effect of the invention of the cited item, further, because the image processing is conducted according to the radiographing information registered together when the discrimination information of the radiation-image storing sheet is registered, the registration mistake of the radiographing information due to the lapse of time as in the case where the radiographing information is registered after the radiographing image is read out can be suppressed, and the correct image processing can be conducted.

According to the present invention, in addition to the effect of the invention of the cited item, further, because the cassette type controller can control the exclusive type radiation-image reading apparatus, and further, the controller can receive the image data outputted by the exclusive radiation-image reading apparatus, in the case where the exclusive type radiation-image reading apparatus and the cassette type radiation-image reading apparatus are installed in the same radiographing room, it is not necessary that respectively different controllers control them, thereby, the number of installations of the controllers, installation area, and apparatus cost can be reduced.

Further, when the same patient is photographed by the exclusive type radiation-image reading apparatus and the cassette type radiation-image reading apparatus, because the registration of the patient information or radiographing information, or image confirmation can be conducted by the same controller, the operation efficiency is increased, and the operation mistake can be reduced.

Disclosed embodiments can be varied by a skilled person without departing from the spirit and scope of the invention.

What is claimed:

1. A photographing system for photographing a patient so as to generate medical image data, and for administrating medical images through a network, comprising:
a plurality of controllers, wherein each controller registers a photographing order for a patient, receives medical image data through the network and has a display to indicate the received medical image data; and
an image data generating section to generate medical image data of a patient in accordance with the photographing order,
wherein the image data generating section specifies a controller having registered a target photographing order for a target patient and sends the medical image data of the target patient to the specified controller through the network so that the specified controller indicates the medical image data of the registered patient.

2. The photographing system of claim 1, further comprising as the image data generating section:
first and second image data generating sections to generate medical image data of a patient in accordance with respective photographing orders,
wherein when a controller registers first and second photographing orders for the same patient, the first image data generating section generates first medical image data of the same patient in accordance with the first photographing order, specifies the controller having registered the first photographing order and sends the first medical image data to the specified controller, and the second image data generating section generates second medical image data of the same patient in accordance with the second photographing order, specifies the controller having registered the second photographing order and sends the second medical image data to the specified controller so that the specified controller indicates both of the first and second medical image data of the registered same patient.

3. The photographing system of claim 2, wherein the first image data generating section is different from the second image data generating section.

4. The radiographing system of claim 3, wherein the data set includes a radiographing condition to designate a body part of the patient and an orientation of the radiographed body part, and wherein each radiation image data generating section generates the radiation image data based on the radiographing condition.

5. The photographing system of claim 3, wherein the first image data generating section is a stationary image data generating station and the second image data generating section is a portable image data generating station.

6. The photographing system of claim 5, wherein each controller sends the data set to each radiation image data generating section, wherein each radiation image data generating section stores the plurality of different data sets in a memory, and wherein each radiation image data generating section retrieves the plurality of different data sets in the memory with the detector ID code of the target radiation image detector and specifies the controller from the controller ID in the data set including the detector ID code of the target radiation image detector.

7. The photographing system of claim 3, wherein the first image data generating section is a standing image data generating station to which photographs a patient in a standing attitude and the second image data generating section is a laying image data generating section which photograph a patient in a laying attitude.

8. The photographing system of claim 1, wherein the photographing system comprises a radiographing system for radiographing the patient so as to generate radiation image data as the medical image data, wherein each controller registers a detector ID code of a radiation image detector to receive a radiation image of a patient, and wherein the image data generating section specifies a controller having registered the target photographing order for the target patient based on a detector ID code of a target radiation image detector.

9. The photographing system of claim 8, wherein each controller has a controller ID and forms a data set including at least a patient ID code, the detector ID code and the controller ID code.

10. The photographing system of claim 9, further comprising a server which receives a plurality of different data sets from the plurality of controllers and stores the plurality of different data sets in a database.

11. The photographing system of claim 10, wherein the radiation image data generating section retrieves the database in the server with the detector ID code of the target radiation image detector and specifies the controller from the controller ID in the data set including the detector ID code of the target radiation image detector.

12. The photographing system of claim 1, further comprising as the image data generating section:
first and second image data generating sections differing in type to generate medical image data of a patient in accordance with respective photographing orders.

13. The photographing system of claim 12, wherein the first image data generating section is a stationary image data generating section and the second image data generating section is a portable image data generating section.

14. The photographing system of claim 12, wherein the first image data generating section is a standing image data generating section which photographs a patient in a standing attitude and the second image data generating section is a laying image data generating section which photographs a patient in a laying attitude.

* * * * *